US012806215B2

(12) United States Patent
Swisa et al.

(10) Patent No.: US 12,806,215 B2
(45) Date of Patent: Nov. 24, 2026

(54) CANNABIDIOLIC ACID ESTERS FOR TREATING PRADER-WILLI SYNDROME

(71) Applicants: EPM (IP), Inc., Florence, KY (US); Yissum Res Dev Co of Hebrew Uni of Jerusalem Ltd., Jerusalem (IL)

(72) Inventors: Reshef Swisa, Santa Monica, CA (US); Rotem Sher, Kibbutz Gal On (IL); Ron Shahrabani, Herzliya (IL); Joseph Tam, Jerusalem (IL)

(73) Assignees: EPM (IP), INC., Florence, KY (US); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 322 days.

(21) Appl. No.: 18/574,167

(22) PCT Filed: Jul. 7, 2022

(86) PCT No.: PCT/IL2022/050734

§ 371 (c)(1),
(2) Date: Dec. 26, 2023

(87) PCT Pub. No.: WO2023/286047

PCT Pub. Date: Jan. 19, 2023

(65) Prior Publication Data

US 2024/0316073 A1 Sep. 26, 2024

Related U.S. Application Data

(60) Provisional application No. 63/276,668, filed on Nov. 8, 2021, provisional application No. 63/221,006, filed on Jul. 13, 2021.

(51) Int. Cl.

| | |
|---|---|
| ***A61K 31/00*** | (2006.01) |
| ***A61K 36/185*** | (2006.01) |
| ***A61P 3/04*** | (2006.01) |
| ***A61P 25/00*** | (2006.01) |

(52) U.S. Cl.
CPC ........ *A61K 31/658* (2023.05); *A61K 36/3482* (2024.05); *A61P 3/04* (2018.01); *A61P 25/00* (2018.01)

(58) Field of Classification Search
CPC .................................................... A61K 31/658
See application file for complete search history.

(56) References Cited

U.S. PATENT DOCUMENTS

| | | | |
|---|---|---|---|
| 5,993,805 A | 11/1999 | Sutton | |
| 6,921,527 B2 | 7/2005 | Platz | |
| 10,588,870 B2 | 3/2020 | Eck | |
| 2018/0028489 A1 | 2/2018 | Vangara | |
| 2023/0059087 A1* | 2/2023 | Zhou | C07C 65/10 |

FOREIGN PATENT DOCUMENTS

| | | | | |
|---|---|---|---|---|
| CN | 113087599 | * | 7/2021 | A61K 31/005 |
| CN | 113087599 | A | 7/2021 | |
| WO | 9916419 | A1 | 4/1999 | |
| WO | 9953917 | A1 | 10/1999 | |
| WO | 0000215 | A1 | 1/2000 | |
| WO | 2017178807 | A1 | 10/2017 | |
| WO | 2018200024 | A1 | 11/2018 | |
| WO | 2018235079 | A1 | 12/2018 | |
| WO | 2020186010 | A1 | 9/2020 | |
| WO | 2021137224 | A1 | 7/2021 | |

OTHER PUBLICATIONS

Butler et al., (2019) Prader-Willi Syndrome—Clinical Genetics, Diagnosis and Treatment Approaches: An Update. Curr Pediatr Rev 15(4): 207-244.
Citti et al., (2018) Analysis of cannabinoids in commercial hemp seed oil and decarboxylation kinetics studies of cannabidiolic acid (CBDA). J Pharm Biomed Anal 149: 532-540.
Grlic (1962) A comparative study on some chemical and biological characteristics of various samples of cannabis resin. Bulletin on Narcotics 14(3): 37-46. 18 pages.
Hen-Shoval et al., (2018) Acute oral cannabidiolic acid methyl ester reduces depression-like behavior in two genetic animal models of depression. Behav Brain Res 351: 1-3.
Krejci and Santavy (1955) Isolation of other substances from the leaves of Indian hemp. Acta Univ Palacki Olomuc 6:59-66. With English summary.
Mechoulam and Ben-Zvi (1969) Carboxylation of resorcinols with methylmagnesium carbonate. Synthesis of cannabinoid acids. J Chem Soc D pp. 343-344.
Mechoulam and Gaoni (1965) Hashish—IV: The isolation and structure of cannabinolic cannabidiolic and cannabigerolic acids. Tetrahedron 21(5): 1223-1229.
Pertwee et al., (2018) Cannabidiolic acid methyl ester, a stable synthetic analogue of cannabidiolic acid, can produce 5-HT1A receptor-mediated suppression of nausea and anxiety in rats. Br J Pharmacol 175(1): 100-112.
Rock et al., (2015) Effect of combined doses of Δ(9)-tetrahydrocannabinol (THC) and cannabidiolic acid (CBDA) on acute and anticipatory nausea using rat (Sprague-Dawley) models of conditioned gaping. Psychopharmacology (Berl) 232(24): 4445-4454.
Rock et al., (2020) Evaluation of repeated or acute treatment with cannabidiol (CBD), cannabidiolic acid (CBDA) or CBDA methyl ester (HU-580) on nausea and/or vomiting in rats and shrews. Psychopharmacology (Berl) 237(9): 2621-2631.

(Continued)

*Primary Examiner* — Paul V Ward
(74) *Attorney, Agent, or Firm* — Ballard Spahr LLP

(57) ABSTRACT

The present invention provides compositions and methods for treating Prader Willi Syndrome (PWS). In particular, the present invention provides pharmaceutical compositions and formulations comprising cannabidiolic acid (CBDA) ester derivatives alone or in combination with one or more additional cannabinoid compound(s), and a pharmaceutically acceptable carrier, excipient or diluent, for use in treating PWS.

20 Claims, 18 Drawing Sheets

(56) References Cited

OTHER PUBLICATIONS

Rock et al., (2021) Therapeutic Potential of Cannabidiol, Cannabidiolic Acid, and Cannabidiolic Acid Methyl Ester as Treatments for Nausea and Vomiting. Cannabis Cannabinoid Res 6(4): 266-274.
Zhu et al., (2020) An evaluation of the anti-hyperalgesic effects of cannabidiolic acid-methyl ester in a preclinical model of peripheral neuropathic pain. Br J Pharmacol 177(12): 2712-2725.
NCT02844933; Cannabidiol Oral Solution for the Treatment of Patients With Prader-Willi Syndrome. First Posted: Jul. 26, 2016. Retrieved from: https://classic.clinicaltrials.gov/ct2/show/NCT02844933?term=NCT02844933&draw=2&rank=1 on Apr. 21, 2024. 8 pages.
Ben-Cnaan et al., (2022) The Metabolic Efficacy of a Cannabidiolic Acid (CBDA) Derivative in Treating Diet- and Genetic-Induced Obesity. Int J Mol Sci 23(10): 5610; 16 pages.
Ning et al., (2020) Application and Development of Non-Psychoactive Medicinal Cannabis. Chinese Journal of Experimental Traditional Medical Formulae 26(8): 228-240. Abstract.
Potter et al., (2008) Potency of delta 9-THC and other cannabinoids in cannabis in England in 2005: implications for psychoactivity and pharmacology. J Forensic Sci 53(1): 90-94. Abstract.
Yu Shenghong (2007) Pathogenesis of Type 1 Diabetes Mellitus. Chinese Journal of Eugenics and Genetics 15(7): 6-7. With machine translation.

* cited by examiner

CANNABIDIOLIC ACID ESTERS FOR TREATING PRADER-WILLI SYNDROME

FIELD OF THE INVENTION

The present invention relates to compositions and methods for treating Prader-Willi Syndrome (PWS). In particular, the present invention relates to pharmaceutical compositions and formulations comprising cannabidiolic acid (CBDA) ester derivatives alone or in combination with one or more additional cannabinoid compound(s), for use in treating PWS.

BACKGROUND OF THE INVENTION

Prader-Willi Syndrome (PWS) is a rare complex multi-system genetic disorder recognized as the most commonly known genetic cause of life-threatening obesity in humans. PWS arises from errors of genomic imprinting with lack of expression of paternally inherited imprinted genes in the chromosome 15q11-q13 region generally caused by a paternal deletion, maternal disomy 15 in which both chromosome 15s are inherited from the mother or from imprinting mutations in 15q11-q13 region. The cardinal clinical features include severe infantile hypotonia, hyperphagia with the onset of obesity during early childhood if not controlled, developmental delay with learning and behavioral problems, short stature with small hands/feet and hypogonadism/hypogenitalism due to growth hormone and other endocrine deficiencies. Mild craniofacial dysmorphism with enamel hypoplasia and a dry mouth are common. Psychiatric phenotypes, behavioral and autism features correlate with specific PWS genetic subtypes (e.g., autism in those with maternal disomy 15). PWS occurs in about 1 in 15,000 individuals (Butler et al. 2019, Curr Pediatr Rev. 2019 November; 15 (4): 207-244).

Cannabidiol (CBD) is the major non-psychotropic phytocannabinoid compound in the plant *Cannabis sativa,* making up to 40% of the cannabinoids in *Cannabis* extracts (Grlic, Bull. Narc., 1976, 14:37-46). CBD is considered a lead compound for treating and preventing inflammatory and oxidative damage, see for example WO1999/053917.

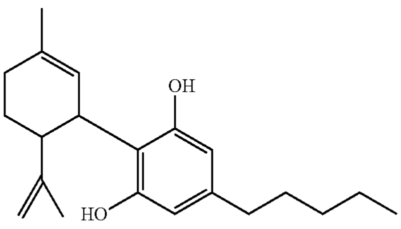

CBD

In contrast to the extensive knowledge on CBD, there is very limited literature on cannabidiolic acid (CBDA), also a major constituent of the *Cannabis sativa* plant, which may be due to its instability. It was first isolated in 1955 (Krejčí and Šantavý, 1955, Acta Univ Palacki Olomuc 6:59-66). Its structure was elucidated in 1965 by analysis of the physical properties of its methyl ester, cannabidiolic acid methyl ester (CBDA-ME) (Mechoulam and Gaoni, Tetrahedron, 1965, 21:1223-1229). Its synthesis from CBD was subsequently reported (Mechoulam and Ben-Zvi, J. Chem. Soc. Commun., 1969, 7:343-344).

The decarboxylation of CBDA into CBD is enhanced by heat, indicating the relative instability of CBDA, thus lowering its potential to serve as a medication (Mechoulam, Academic Press, New York, 1973, 1-99; Citti et al., J. Pharm. Biomed. Anal., 2018, 16:532-540). Thus, CBDA-ME is a relatively unknown cannabinoid and remains understudied and its effects are only just starting to become clear.

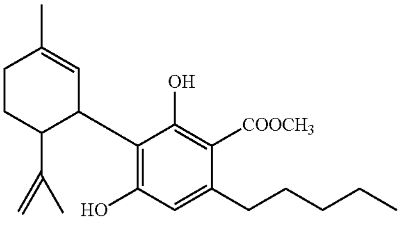

CBDA-ME

CBDA-ME is a derivative of CBDA and can be pharmacological active in vivo. Pertwee et al. (Brit. J. Pharmacology, 2018, 175:100-112) reported that the methyl ester of CBDA, designated HU-580 (also denoted herein EPM301), displays a greater potency than CBDA in suppressing signs of both acute and anticipatory nausea, and of stress-induced anxiety in rats, and that it produces these effects in a 5-$HT_{1A}$ receptor-dependent manner. Another recent study (Hen-Shoval et al., Behav. Brain Res., 2018, 351:1-3) provides support for a potent anti-depressant effect after oral ingestion of a low dose (1 mg/kg) of CBDA-ME in two rat models.

WO 2018/235079 discloses compositions comprising CBDA esters and uses thereof in the treatment of a condition, disease or symptom associated with 5-$HT_{1A}$ receptors.

WO 2020/186010 discloses pharmaceutical compositions including a cannabinoid acid ester compound alone or in combination with one or more additional cannabinoid compounds. The PCT application discloses the uses of the pharmaceutical compositions in treating a variety of diseases including joint disease, skin disease, gastrointestinal disease, uterine-related disorder, non-alcoholic fatty liver disease (NAFLD), chronic kidney disease (CKD), diabetes, dyslipidemia, metabolic syndrome, hyperglycemia, obesity, and reducing or maintaining cholesterol levels or lowering LDL/HDL ratio.

CBD oral solution was suggested for the treatment of subjects with PWS and tested in a phase 2 clinical trial [https://www.clinicaltrials.gov/ct2/show/NCT02844933?term=insys].

There still an unmet medical need for well-tole rated, and effective therapies for PWS that can ameliorate its symptoms.

SUMMARY OF THE INVENTION

The present invention provides pharmaceutical compositions comprising a cannabinoid, wherein the cannabinoid component comprises a cannabidiolic acid (CBDA) ester alone or in combination with one or more additional cannabinoid compound(s), and a pharmaceutically acceptable carrier, excipient or diluent, for treating Prader Willi Syndrome. According to certain embodiments the cannabinoid component comprises CBDA ester in combination with one or more extract of a *Cannabis* plant, and a pharmaceutically acceptable carrier, excipient or diluent.

In some embodiments, the CBDA esters are more active in treating PWS than either CBDA or CBD. The compositions comprising CBDA esters exhibit a prolonged and significant therapeutic effect in PWS. Without wishing to be bound by any particular theory or mechanism of action, the therapeutic effect of the composition may be due to the stability of the CBDA ester.

It is now disclosed that treatment with CBDA-ME reduces body weight, reduces fat mass (while maintaining lean mass), improves ambulatory activity, normalizes lipid, glucose and insulin levels, reduces fat in the liver, and improves liver enzyme levels in a mouse model for PWS (Magel2 null mice).

According to one aspect, the present invention provides a pharmaceutical composition comprising a cannabinoid component, wherein the cannabinoid component comprises a CBDA ester represented by the structure of Formula (I) alone or in combination with one or more additional cannabinoid compound(s), and a pharmaceutically acceptable carrier, excipient or diluent, for use in treating PWS, Formula (I)

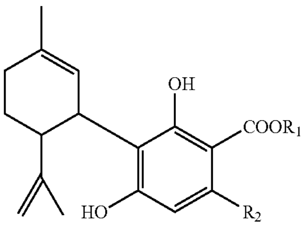

wherein $R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

According to some embodiments, $R_1$ is methyl. According to some embodiments, the cannabidiolic acid ester is CBDA-ME.

According to some embodiments, the CBDA ester in the compositions of the present invention is represented by Formula (Ia):

Formula (Ia)

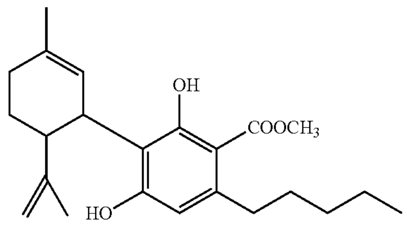

According to some embodiments, the CBDA ester in the compositions of the present invention is represented by the Formula (Ib):

Formula (Ib)

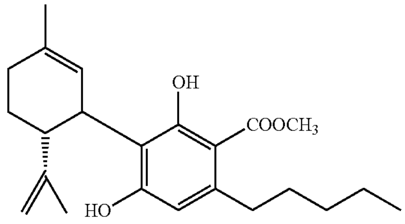

According to a particular embodiment, the CBDA ester is (designated herein EPM301):

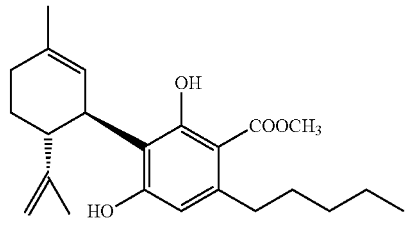

According to some embodiments, the pharmaceutical composition is for use in slowing down, preventing progression of, treating or ameliorating one or more symptoms of PWS.

According to some embodiments, the pharmaceutical composition comprises the additional cannabinoid compound. According to some embodiments, the additional cannabinoid compound is selected from the group consisting of CBD, cannabigerol (CBG), $\Delta^8$-tetrahydrocannabinol ($\Delta^8$-THC), $\Delta^9$-tetrahydrocannabinol ($\Delta^9$-THC), cannabinol (CBN), $\Delta^9$ (11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof and combination thereof.

According to some embodiments the one or more additional cannabinoid compound(s) are present in one or more extracts of a *Cannabis* plant. According to some embodiments the one or more additional cannabinoid compound(s) are obtained from one or more extracts of a *Cannabis* plant.

According to some embodiments, the *Cannabis* plant extract is obtained from a species or strain selected from the group consisting of *Cannabis sativa, Cannabis indica, Cannabis ruderalis,* a hybrid strain, and combinations thereof. According to further embodiments, the *Cannabis* plant extract is obtained from a strain selected from the group consisting of a high-CBD strain, a high-THC strain, and a combination thereof. According to some embodiments, the *Cannabis* plant extract comprises at least one cannabinoid selected from the group consisting of CBD, THC, CBN, CBG, CBC, acids thereof and combinations thereof.

According to some embodiments, the *Cannabis* plant extract comprises about 1% (w/w) CBD. According to some embodiments, the *Cannabis* plant extract comprises about 10% (w/w) CBD. According to some embodiments, the *Cannabis* plant extract comprises about 25% (w/w) CBD.

According to some embodiments, the *Cannabis* plant extract comprises about 1% (w/w) THC. According to some embodiments, the *Cannabis* plant extract comprises about 10% (w/w) THC. According to some embodiments, the *Cannabis* plant extract comprises about 25% (w/w) THC.

According to some embodiments, the *Cannabis* plant extract is formed through contact with a suitable solvent or a combination of solvents. According to some embodiments, the solvent is selected from the group consisting of a polar solvent, a hydrocarbon solvent, carbon dioxide, and combinations thereof.

According to some embodiments, the pharmaceutical composition is in the form of an emulsion, solution, gel or dispersion. According to some embodiments, the pharmaceutically acceptable carrier, excipient or diluent comprises water, oil, or both. Each possibility represents a separate embodiment of the present invention.

According to some embodiments, the cannabinoid component can be emulsified, dissolved, dispersed or encapsulated in formulations suitable for use in either aqueous based or oil-based carriers. Thus, according to some embodiments, the present pharmaceutical composition is in the form of an emulsion, solution or dispersion. Each possibility represents a separate embodiment. Also, according to some embodiments, the present pharmaceutical composition may include an aqueous based or an oil-based carrier. Each possibility represents a separate embodiment.

According to some embodiments, the pharmaceutical composition is formulated for inhalation. According to specific embodiments, the pharmaceutical composition is a dry powder formulation. According to some embodiments, the pharmaceutical composition is formulated for an administration via vaporization.

According to alternative embodiments, the pharmaceutical composition is formulated into a dosage form suitable for intranasal, oral, intravenous, intraarterial, or subcutaneous administration. Each embodiment represents a separate embodiment of the invention. According to additional embodiments, the pharmaceutical composition is formulated for an oral administration.

According to some embodiments, the pharmaceutical composition is a non-aqueous composition. It is to be understood that non-aqueous compositions may include any dry composition or composition, which comprises a non-aqueous solvent or additive, and includes no more than 10%, no more than 5%, no more than 2% or no more than 1% water (w/w). According to some embodiments, the pharmaceutical composition is formulated in a form of a powder. According to some embodiments, the pharmaceutical composition is powder suitable for multi-dose reservoir dry powder inhaler (DPI).

According to other embodiments, the pharmaceutical composition is a liquid composition.

According to some embodiments, the pharmaceutical composition is formulated as a capsule, a tablet, a liquid, or a syrup. According to certain embodiments, the dosage form is granules or pellets delivered in a solution, a suspension or filled into a capsule or compressed into a tablet.

According to some embodiments, the pharmaceutical composition further comprises triglycerides, fats, lipids, oils, fatty acids, solvents or mixtures thereof. According to some embodiments, the excipient is selected from the group consisting of triglycerides, fats, lipids, oils, fatty acids, solvents or mixtures thereof. According to specific embodiments, the pharmaceutical composition comprises an edible oil selected from the group consisting of copaiba oil, coconut oil, cottonseed oil, soybean oil, safflower oil, sesame oil, sunflower oil, castor oil, corn oil, olive oil, palm oil, peanut oil, and poppy seed oil. Each possibility represents a separate embodiment of the invention.

According to some embodiments, the pharmaceutical composition comprises an alcohol. According to some embodiments, the pharmaceutical composition comprises an alcohol and a second solvent. According to some embodiments, the alcohol is ethanol. According to certain embodiments, the second solvent is polyethylene glycol (PEG), propylene glycol or both. Each possibility represents a separate embodiment of the present invention.

According to some embodiments, the pharmaceutical composition is formulated for slow release of the CBDA ester. In certain embodiments, the pharmaceutical composition further comprises a release retarding agent or a mixture of release retarding agents. According to some embodiments, the pharmaceutical composition is at least partly coated by an enteric-coating agent.

According to some embodiments, the CBDA ester is provided in microencapsulation particles. According to certain embodiments, the CBDA ester is provided in liposomal capsule particles.

According to some embodiments, the pharmaceutical composition comprises phospholipid(s). According to certain embodiments, the pharmaceutical composition comprises a phospholipid selected from the group consisting of naturally occurring phospholipids and synthetic phospholipids. According to specific embodiments, the naturally occurring phospholipid is selected from the group consisting of soy lecithin, egg lecithin, hydrogenated soy lecithin, hydrogenated egg lecithin, and a combination thereof. According to certain embodiments, the synthetic phospholipid is selected from the group consisting of phosphocholines, phosphoethanolamines, phosphatidic acids, phosphoglycerols, phosphoserines, mixed chain phospholipids, lysophospholipids, pegylated phospholipids, and a combination thereof. Each possibility represents a separate embodiment of the invention.

According to some embodiments, the phospholipid may form micelles, emulsions or liposomes. According to some embodiments, the phospholipid forms micelles, emulsions or liposomes. According to some embodiments, the pharmaceutical composition is in the form of a micelle, an emulsion or a liposome According to some embodiments, the pharmaceutical composition comprises a cyclodextrin. According to certain embodiments, the cyclodextrin is selected from the group consisting of hydroxypropyl β-cyclodextrin, sulfobutylether β-cyclodextrin, and methyl-β-cyclodextrin (MβCD) and a combination thereof. Each possibility represents a separate embodiment of the invention.

According to some embodiments, the excipient is selected from the group consisting of emulsifiers, buffering agents, pH adjusting agents, preservatives, antioxidants, stabilizers, and a combination thereof. Each possibility represents a separate embodiment of the invention.

According to some embodiments, the pharmaceutical composition further comprises vitamins, anti-oxidants, minerals, and/or flavoring agents.

According to some embodiments, the composition comprises less than about 10% (w/w) of the cannabinoid component. According to additional embodiments, the composition comprising less than about 7% (w/w) of the cannabinoid component. According to further embodiments, the composition comprising less than about 5% (w/w) of the cannabinoid component. According to yet further embodiments, the composition comprising less than about 2% (w/w) of the cannabinoid component. According to some embodiments, the composition comprising less than about 1% (w/w) of the cannabinoid component. According to additional embodiments, the composition comprising less than about 0.5% (w/w) of the cannabinoid component.

According to some embodiments, the pharmaceutical composition comprises a unit dosage form of at least about 20 mg of the CBDA ester. In certain embodiments, the dosage form comprises about 20 mg to about 2,000 mg of the CBDA ester. In certain embodiments, the dosage form comprises about 20 mg to about 500 mg of the CBDA ester. In certain embodiments, the dosage form comprises about 50 mg to about 1,000 mg of the CBDA ester. In certain embodiments, the dosage form comprises about 200 mg to about 1,000 mg of the CBDA ester. In certain embodiments, the dosage form comprises about 50 mg, 100 mg, about 200 mg, about 300 mg, about 400 mg, about 500 mg, about 600, about 700 mg, about 800 mg, about 900 mg, about 1000 mg, about 2000 mg, about 3000, about 4000, about 5000 mg, about 6000, about 8000 or about 10000 mg of the CBDA ester. Each possibility represents a separate embodiment of the present invention. According to some embodiments, the pharmaceutical composition comprises a unit dosage form of at least about 20 mg of the cannabinoid component. In certain embodiments, the dosage form comprises about 20 mg to about 2,000 mg of the cannabinoid component. In certain embodiments, the dosage form comprises about 20 mg to about 500 mg of the cannabinoid component. In certain embodiments, the dosage form comprises about 50 mg to about 1,000 mg of the cannabinoid component. In certain embodiments, the dosage form comprises about 200 mg to about 1,000 mg of the cannabinoid component. In certain embodiments, the dosage form comprises about 50 mg, 100 mg, about 200 mg, about 300 mg, about 400 mg, about 500 mg, about 600 mg, about 700 mg, about 800 mg, about 900 mg, about 1000 mg, about 2000 mg, or about 5000 mg of the cannabinoid component. Each possibility represents a separate embodiment of the present invention.

The pharmaceutical composition described herein can be administered with one or more other therapeutic agents. According to some embodiments, the pharmaceutical composition further comprises at least one additional therapeutic agent for treatment PWS.

According to an additional aspect, the present invention provides a method for treating PWS comprising administering to a subject in need of such treatment a therapeutically effective amount of the pharmaceutical composition described herein.

According to some embodiments, the treating comprises slowing down, preventing progression of, treating or ameliorating one or more symptoms of PWS.

According to some embodiments, the treating comprises treating behaviors associated with PWS.

According to certain embodiments, the treating results in one or more of: (a) decrease in obsessive and compulsive behavior compared to placebo; or (b) decrease in anxiety compared to placebo.

According to some embodiments, the treating results in reducing or eliminating a constant feeling of hunger, reducing or eliminating excessive appetite (hyperphagia), reducing or eliminating weight gain, reducing or eliminating obesity. According to certain exemplary embodiments, the treating results in a decrease in measurement of Hyperphagia Questionnaire for Clinical Trials (HQ-CT) Total Score.

According to some embodiments, the pharmaceutical composition is administered through inhalation from a vaporizer or metered dose inhaler. According to other embodiments, the pharmaceutical composition is administered orally.

According to some embodiments, the pharmaceutical composition is administered once a day, once a week, once in two weeks, once in three weeks or once a month.

According to some embodiments, the subject is a mammal. According to certain embodiments, the subject is a human subject.

According to some embodiments, the pharmaceutical composition is administered through inhalation from a vaporizer or metered dose inhaler. According to other embodiments, the pharmaceutical composition is administered orally.

According to some embodiments, the pharmaceutical composition is administered once a day, once a week, once in two weeks, once in three weeks or once a month.

According to some embodiments, the subject is a mammal. According to certain embodiments, the subject is a human subject.

According to some embodiments, the pharmaceutical composition is used in combination with other therapeutic agents for treatment of PWS.

According to some embodiments, the method further comprises administering insulin, an insulin receptor agonist, Growth hormone-releasing hormone (GHRH), a GHRH receptor agonist, alpha-Melanocyte-stimulating hormone ($\alpha$MSH), an alpha-MSH receptor agonist, oxytocin, an oxytocin receptor agonist, orexin, an orexin receptor agonist, Brain-derived neurotrophic factor (BDNF), a BDNF receptor agonist, vasopressin, a vasopressin receptor agonist, Neuropeptide Y (NPY), an NPY receptor agonist, Agouti Related Neuropeptide (AGRP), an AGRP receptor agonist, gonadotropin, a gonadotropin receptor against, or combinations thereof. Each possibility represents a separate embodiment of the invention.

According to some embodiments, the treating improves at least one of PWS associated symptom selected from the group consisting of hyperphagia, reduced metabolic rate, obesity, hypogonadism, decreased growth hormone production, poor muscle tone, reduced stamina, reduced ability to focus, impaired cognition, anxiety, growth failure, reduced conversion of immature hormones to mature and active forms, diabetes and any combinations thereof. Each possibility represents a separate embodiment of the invention.

According to some embodiments, the treating improves muscle tone. In some embodiments, the treating improves sucking reflex.

Further embodiments and the full scope of applicability of the present invention will become apparent from the detailed description and drawings given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 8C shows histology images of the liver with or without treatments in WT or PWS mouse model fed with high-fat diet (HFD).

DETAILED DESCRIPTION OF THE INVENTION

Figure 1A:
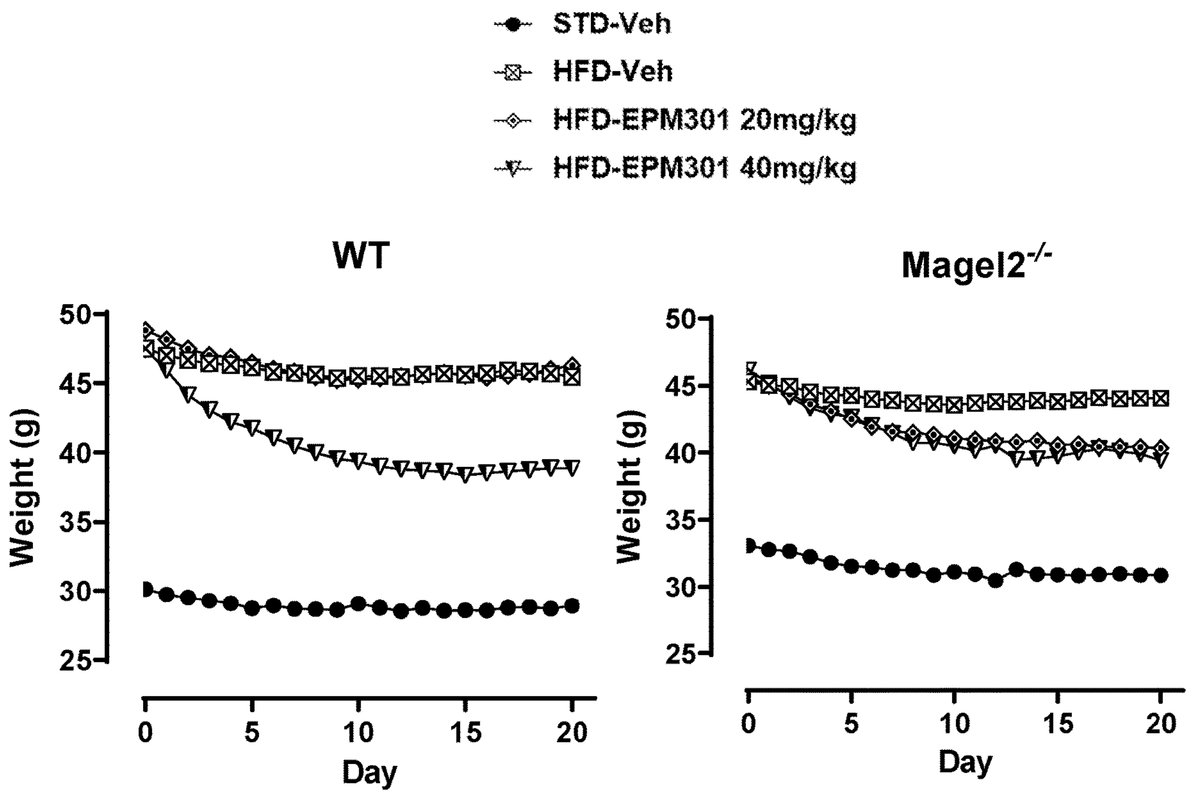
FIGS. 1A-1F show the effect of different doses of CBDA-ME (EPM301) on body weight of WT or PWS mouse model when fed with a high-fat diet (HFD).
Figure 1B:
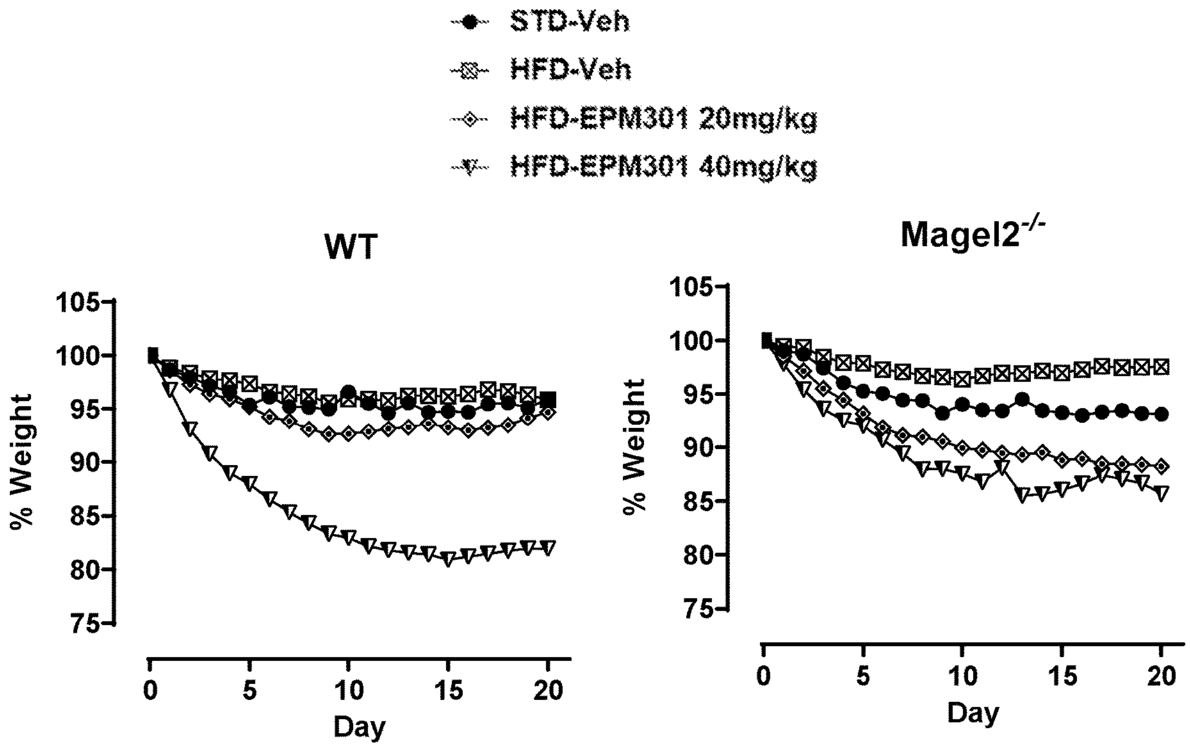
Figure 1C:
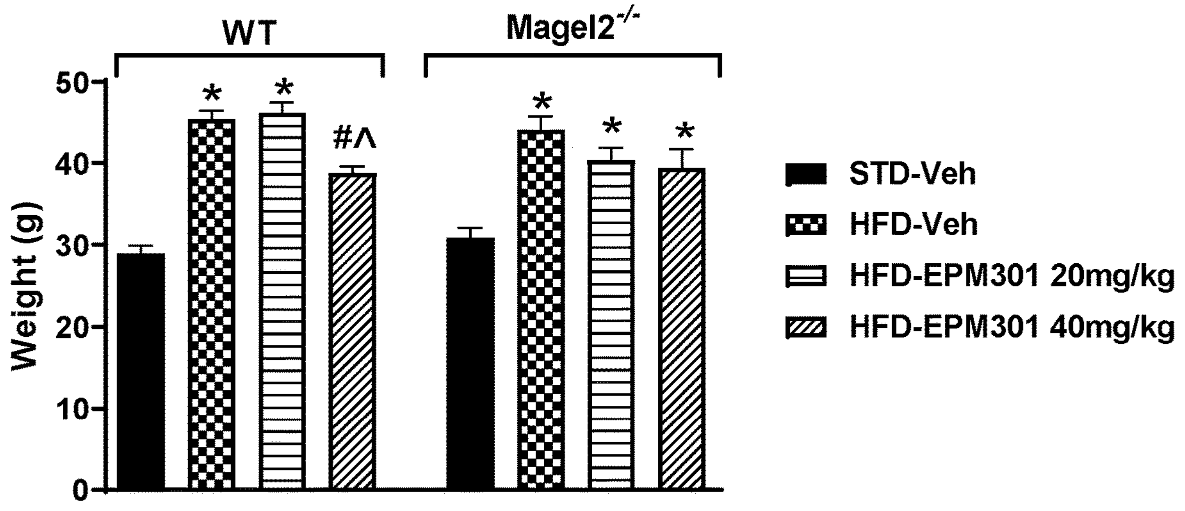
Figure 1D:
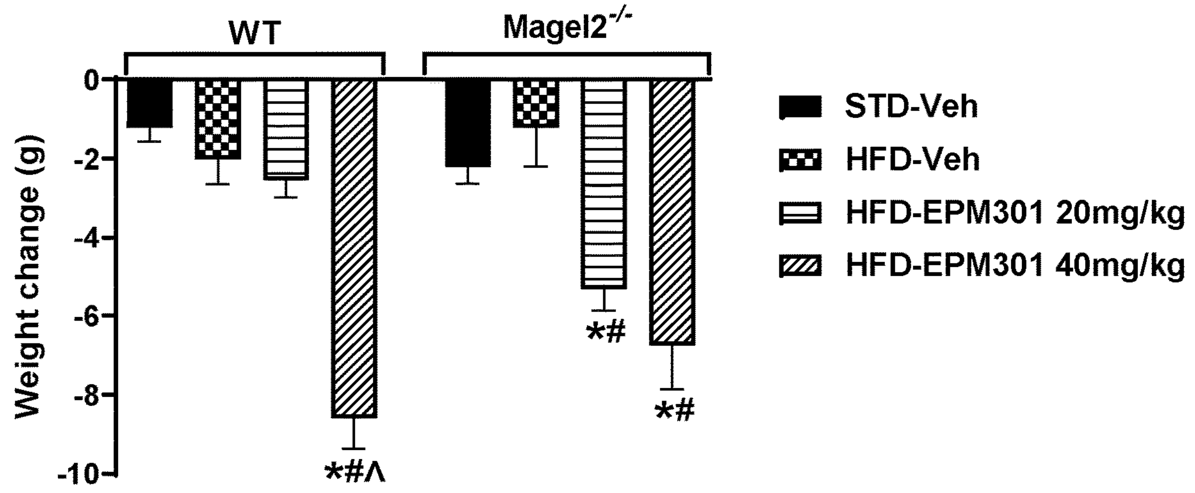
Figure 1E:
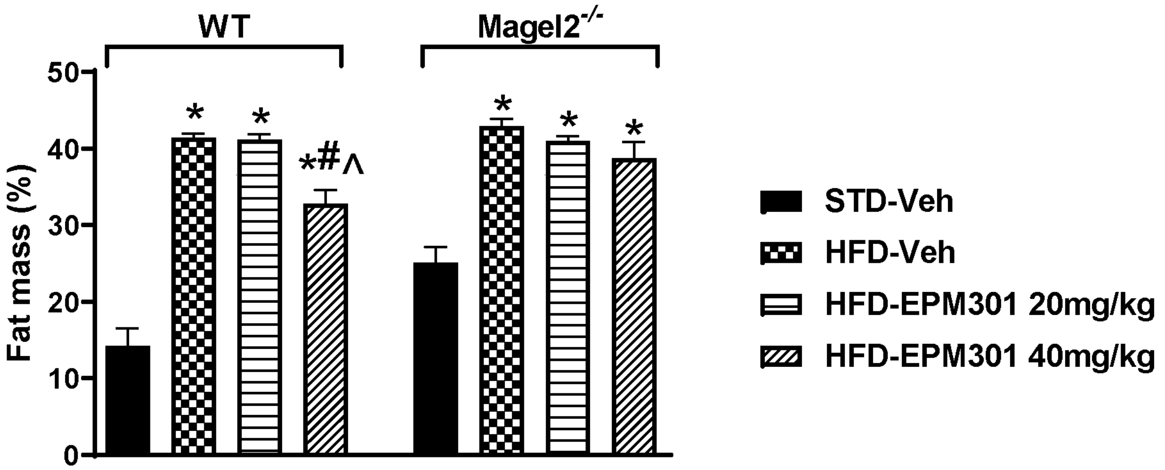

The present invention provides methods of treating PWS, comprising administering to a subject in need thereof a therapeutic effective amount of a CBDA ester alone or in combination with one or more additional cannabinoid compound(s), and a pharmaceutically acceptable carrier, excipient or diluent.

Without wishing to be bound by theory or mechanism of action, the highly stable compounds of the present invention allow prolonged biological activities for treating PWS.

PWS is caused by a loss of paternally expressed genes in an imprinted region of chromosome 15q. Subjects with PWS typically suffer from a variety of symptoms including neurologic, cognitive, endocrine, and behavioral abnormalities. Initially, infants exhibit hypotonia (floppy baby syndrome) and experience difficulty in sucking and feeding which can lead to growth delay. Subjects with PWS frequently have poor muscle tone, growth hormone deficiency, low levels of sex hormones, a constant feeling of hunger and excessive appetite (hyperphagia). They overeat, leading to weight gain, obesity and a high incidence of diabetes. Other signs appear including short stature, poor motor skills, underdeveloped sex organs, and mild intellectual and learning disabilities. PWS subjects may experience delayed speech and language development, and infertility. Behavioral symptoms may include cognitive impairment, cognitive rigidity, emotional lability and obsessive-compulsive behavior, with autistic symptomology, psychotic episodes, and biopolar disorder with psychosis. Additional clinical manifestations may include excessive daytime sleepiness, scoliosis, osteopenia/osteoporosis, decreased gastrointestinal motility, sleep disturbances, and reduced pain sensitivity.

The description below of several embodiments are made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

Cannabinoid Component

The word "cannabinoid" used in this description, claims, and other conjugations is used to mean any compound that interacts with a cannabinoid receptor. Ligands for these receptor proteins include the endocannabinoids (produced naturally in the body by humans and animals), the phytocannabinoids (found in *Cannabis* and some other plants), and synthetic cannabinoids (manufactured artificially). The term "cannabinoid acid", refers to the acid form of the above-mentioned cannabinoids.

Suitable cannabinoids include but are not limited to certain tetrahydropyran analogs: THC, CBN, CBD, CBG, $\Delta^9$(11)-tetrahydrocannabinol (exo-THC), CBC, tetrahydrocannabinol-C3 (THC-C3), tetrahydrocannabinol-C4 (THC-C4), tetrahydrocannabinol-C7 (THC-C7), their salts, solvates, metabolites, and metabolic precursors.

The word "cannabidiol" refers to CBD. As used in this application, CBD is obtained from industrial hemp extract with a trace amount of THC or from *Cannabis* extract using high CBD *Cannabis* cultivars. According to some embodiments, cannabidiol may be obtained from plant extract, or may be prepared synthetically (manufactured artificially).

The abbreviation "CBDA" is used herein to refer to cannabidiolic acid, which is the carboxylic acid form of CBD. The term "cannabidiolic acid ester" or "cannabidiolic ester" refers to various molecules, which are the alkyl, alkenyl, alkynyl or aryl ester form of CBDA. The abbreviation "CBDA-ME" is used herein to refer to cannabidiolic acid methyl ester, which is the methyl ester form of CBDA.

It is to be understood that although the common CBDA isomers include an n-$C_5H_{11}$ chain at position 2, derivatives of CBDA may include other substituents, in particular alkyl, alkenyl or alkynyl groups. Therefore, the terms cannabidiolic acid and CBDA ester include corresponding structures, in which position 2 is substituted by a group, which is either an n-$C_5H_{11}$ or a different chemical group, in particular alkyl, alkenyl or alkynyl groups. The term "cannabidiolic acid" and/or "cannabidiolic acid ester" should be interpreted broadly referring to all possible stereoconfigurations and salts of the relevant formula.

It is to be understood that the compounds provided herein may contain one or more chiral centers. Such chiral centers may each be of either of the (R) or (S) configuration. In case a compound of the invention contains more than one chiral center, each one of those chiral centers may be of the (R) or (S) configuration, independently. Thus, the compounds provided herein may be enantiomerically pure, or be stereoisomeric or diastereomeric mixtures.

According to an aspect, the present invention provides a pharmaceutical composition comprising a cannabinoid, wherein the cannabinoid component comprises a CBDA ester represented by the structure of Formula (I) alone or in combination with one or more additional cannabinoid compound(s), and a pharmaceutically acceptable carrier, excipient or diluent, for use in treating or PWS, Formula (I)

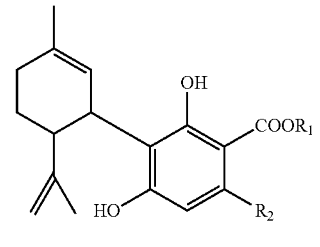

wherein $R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

According to another aspect, the present invention provides a pharmaceutical composition comprising a cannabinoid, wherein the cannabinoid component comprises a CBDA ester represented by the structure of Formula (I) alone or in combination with one or more additional cannabinoid compound(s), and a pharmaceutically acceptable carrier, excipient or diluent, for use in treating PWS, Formula (I)

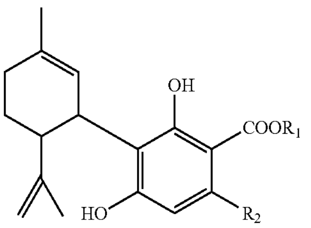

wherein $R_1$ and $R_2$ are each independently selected from the group consisting of a linear or branched $C_1$-$C_{15}$ alkyl unsubstituted or substituted by one or more groups selected from the group consisting of hydroxyl, halogen, amino, thiol, and phosphate, a linear or branched $C_2$-$C_{15}$ alkenyl unsubstituted or substituted by one or more groups selected from the group consisting of hydroxyl, halogen, amino, thiol, and phosphate, and a linear or branched $C_2$-$C_{15}$ alkynyl unsubstituted or substituted by one or more groups selected from the group consisting of hydroxyl, halogen, amino, thiol, and phosphate;

and stereoisomers and salts thereof.

According to an aspect, the present invention provides a pharmaceutical composition comprising a cannabinoid, wherein the cannabinoid component comprises a CBDA ester represented by the structure of Formula (I) alone or in combination with one or more additional cannabinoid compound(s), and a pharmaceutically acceptable carrier, excipient or diluent, for use in treating PWS, Formula (I)

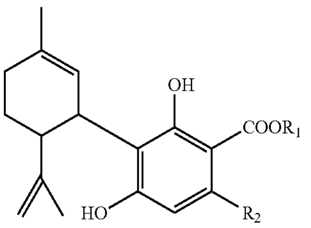

wherein $R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

In certain embodiments the one or more additional cannabinoid compound(s) are present in one or more extracts of a *Cannabis* plant. In certain embodiments the one or more additional cannabinoid compound(s) are provided from one or more extracts of a *Cannabis* plant. In certain embodiments the one or more additional cannabinoid compound(s) are extracted from a *Cannabis* plant(s).

According to some embodiments, $R_1$ is a linear or branched, substituted or unsubstituted $C_1$-$C_{15}$ alkyl. According to some embodiments, $R_1$ is a linear or branched, substituted or unsubstituted $C_1$-$C_{10}$ alkyl. According to some embodiments, $R_1$ is a linear or branched, substituted or unsubstituted $C_5$-$C_{10}$ alkyl. According to some embodiments, $R_1$ is a linear or branched, substituted or unsubstituted $C_5$-$C_{15}$ alkyl. According to some embodiments, $R_1$ is a linear or branched, substituted or unsubstituted $C_2$-$C_{15}$ alkenyl. According to some embodiments, $R_1$ is a linear or branched, substituted or unsubstituted $C_2$-$C_{10}$ alkenyl. According to some embodiments, $R_1$ is a linear or branched, substituted or unsubstituted $C_5$-$C_{10}$ alkenyl. According to some embodiments, $R_1$ is a linear or branched, substituted or unsubstituted $C_5$-$C_{15}$ alkenyl. According to some embodiments, $R_1$ is a linear or branched, substituted or unsubstituted $C_2$-$C_{15}$ alkynyl. According to some embodiments, $R_1$ is a linear or branched, substituted or unsubstituted $C_2$-$C_{10}$ alkynyl. According to some embodiments, $R_1$ is a linear or branched, substituted or unsubstituted $C_5$-$C_{10}$ alkynyl. According to some embodiments, $R_1$ is a linear or branched, substituted or unsubstituted $C_5$-$C_{15}$ alkynyl.

According to some embodiments, $R_1$ is a linear substituted $C_1$-$C_{15}$ alkyl. According to some embodiments, $R_1$ is a linear unsubstituted $C_1$-$C_{15}$ alkyl. According to some embodiments, $R_1$ is a branched substituted $C_3$-$C_{15}$ alkyl. According to some embodiments, $R_1$ is a branched unsubstituted $C_3$-$C_{15}$ alkyl.

According to some embodiments, $R_1$ is a linear substituted $C_2$-$C_{15}$ alkenyl. According to some embodiments, $R_1$ is a linear unsubstituted $C_2$-$C_{15}$ alkenyl. According to some embodiments, $R_1$ is a branched substituted $C_3$-$C_{15}$ alkenyl. According to some embodiments, $R_1$ is a branched unsubstituted $C_3$-$C_{15}$ alkenyl.

According to some embodiments, $R_1$ is a linear substituted $C_2$-$C_{15}$ alkynyl. According to some embodiments, $R_1$ is a linear unsubstituted $C_2$-$C_{15}$ alkynyl. According to some embodiments, $R_1$ is a branched substituted $C_4$-$C_{15}$ alkynyl. According to some embodiments, $R_1$ is a branched unsubstituted $C_4$-$C_{15}$ alkynyl.

According to some embodiments, $R_1$ is unsubstituted. According to some embodiments, $R_1$ is a linear unsubstituted $C_1$-$C_{10}$ alkyl. According to some embodiments, $R_1$ is a linear unsubstituted $C_1$-$C_6$ alkyl. According to some embodiments, $R_1$ is a linear unsubstituted $C_1$-$C_4$ alkyl. According to some embodiments, $R_1$ is methyl or ethyl. According to some embodiments, $R_1$ is methyl.

According to some embodiments, $R_2$ is a linear or branched, substituted or unsubstituted $C_1$-$C_{15}$ alkyl. According to some embodiments, $R_2$ is a linear or branched, substituted or unsubstituted $C_1$-$C_{10}$ alkyl. According to some embodiments, $R_2$ is a linear or branched, substituted or unsubstituted $C_5$-$C_{10}$ alkyl. According to some embodiments, $R_2$ is a linear or branched, substituted or unsubstituted $C_5$-$C_{15}$ alkyl. According to some embodiments, $R_2$ is a linear or branched, substituted or unsubstituted $C_2$-$C_{15}$ alkenyl. According to some embodiments, $R_2$ is a linear or branched, substituted or unsubstituted $C_2$-$C_{10}$ alkenyl. According to some embodiments, $R_2$ is a linear or branched, substituted or unsubstituted $C_5$-$C_{10}$ alkenyl. According to some embodiments, $R_2$ is a linear or branched, substituted or unsubstituted $C_5$-$C_{15}$ alkenyl. According to some embodiments, $R_2$ is a linear or branched, substituted or unsubstituted $C_2$-$C_{15}$ alkynyl. According to some embodiments, $R_2$ is a linear or branched, substituted or unsubstituted $C_2$-$C_{10}$ alkynyl. According to some embodiments, $R_2$ is a linear or branched, substituted or unsubstituted $C_5$-$C_{10}$ alkynyl. According to some embodiments, $R_2$ is a linear or branched, substituted or unsubstituted $C_5$-$C_{15}$ alkynyl.

According to some embodiments, $R_2$ is a linear substituted $C_1$-$C_{15}$ alkyl. According to some embodiments, $R_2$ is a linear unsubstituted $C_1$-$C_{15}$ alkyl. According to some embodiments, $R_2$ is a branched substituted $C_3$-$C_{15}$ alkyl. According to some embodiments, $R_2$ is a branched unsubstituted $C_3$-$C_{15}$ alkyl.

According to some embodiments, $R_2$ is a linear substituted $C_2$-$C_{15}$ alkenyl. According to some embodiments, $R_2$ is a linear unsubstituted $C_2$-$C_{15}$ alkenyl. According to some embodiments, $R_2$ is a branched substituted $C_3$-$C_{15}$ alkenyl. According to some embodiments, $R_2$ is a branched unsubstituted $C_3$-$C_{15}$ alkenyl.

According to some embodiments, $R_2$ is a linear substituted $C_2$-$C_{15}$ alkynyl. According to some embodiments, $R_2$ is a linear unsubstituted $C_2$-$C_{15}$ alkynyl. According to some embodiments, $R_2$ is a branched substituted $C_4$-$C_{15}$ alkynyl. According to some embodiments, $R_2$ is a branched unsubstituted $C_4$-$C_{15}$ alkynyl.

According to some embodiments, $R_2$ is a linear unsubstituted $C_1$-$C_6$ alkyl. According to some embodiments, $R_2$ is a linear unsubstituted $C_1$-$C_4$ alkyl. According to some embodiments, $R_2$ is $C_5H_{11}$.

According to some embodiments, the CBDA ester in the compositions of the present invention is represented by the Formula (Ia):

Formula (Ia)

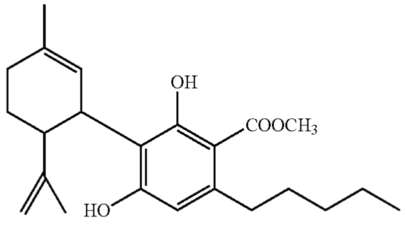

According to some embodiments, the CBDA ester in the compositions of the present invention is represented by the Formula (Ib):

Formula (Ib)

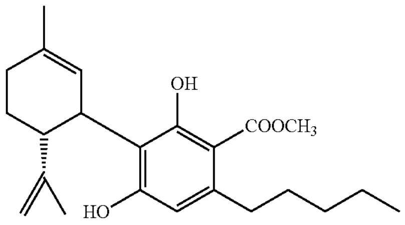

According to a particular embodiment, the CBDA ester is the compound designated EPM301:

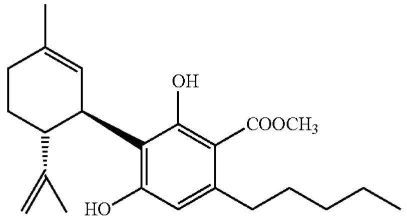

EPM-301

An "alkyl" group refers to a saturated aliphatic hydrocarbon, including straight-chain or linear-chain, branched-chain and cyclic alkyl groups. In one embodiment, the alkyl group has 1-15 carbons designated here as $C_1$-$C_{15}$ alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. Each possibility represents a separate embodiment of the invention. The alkyl group may be unsubstituted or substituted by one or more groups selected from the group consisting of hydroxyl, halogen, amino, thiol, phosphate, and combinations thereof. Thus, the phrase "unsubstituted or substituted alkyl" refers to an alkyl group which is either unsubstituted (i.e. it is a hydrocarbon) or to an alkyl substituted with at least one of hydroxyl, halogen, amino, thiol, phosphate, and combinations thereof.

The terms "halo" and "halogen" refer to the fluoro, chloro, bromo or iodo atoms. Whenever a compound is said to be halogen substituted, the compound may include one or more halogens, which are the same or different.

An "alkenyl" group refers to an aliphatic hydrocarbon group containing at least one carbon-carbon double bond including straight-chain or linear-chain, branched-chain and cyclic alkenyl groups. In one embodiment, the alkenyl group has 2-15 carbon atoms (a $C_{2-15}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl. Thus, the phrase "unsubstituted or substituted alkenyl" refers to an alkenyl group which is either unsubstituted (i.e. it is a hydrocarbon) or to an alkenyl substituted with at least one of hydroxyl, halogen, amino, thiol, phosphate, and combinations thereof.

An "alkynyl" group refers to an aliphatic hydrocarbon group containing at least one carbon-carbon triple bond including straight-chain and branched-chain. In one embodiment, the alkynyl group has 2-15 carbon atoms in the chain (a $C_{2-15}$ alkynyl). In another embodiment, the alkynyl group has 2-4 carbon atoms in the chain (a $C_{2-4}$ alkynyl). Exemplary alkynyl groups include, but are not limited to, ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl. Thus, the phrase "unsubstituted or substituted alkynyl" refers to an alkynyl group which is either unsubstituted (i.e. it is a hydrocarbon)

or to an alkynyl substituted with at least one of hydroxyl, halogen, amino, thiol, phosphate, and combinations thereof.

According to some embodiments, the additional cannabinoid compound is selected from the group consisting of CBD, CBG, $\Delta^8$-THC, $\Delta^9$-THC, CBN, exo-THC, CBC, THC-C3, THC-C4, THC-C7, esters thereof and combination thereof.

It is contemplated that the CBDA ester of Formula (I) or the cannabinoid compound includes any solvate thereof. The term "solvate" as used herein refers to a physical association of a compound disclosed herein with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. A "hydrate" is a solvate in which the solvent molecule is water.

In embodiments in which the CBDA ester is incorporated into a composition in solid state form, the present disclosure also includes any polymorph thereof. The term "polymorph" refers to a particular crystalline or amorphous state of a substance, which can be characterized by particular physical properties such as X-ray diffraction, electron diffraction, IR spectra, Raman spectra, melting point, and the like.

Any of the cannabinoids disclosed herein, specifically, the CBDA ester of Formula (I), can be prepared by any manner known to those skilled in the art. For example, it may be isolated or extracted from a natural source or prepared by synthetic or semi-synthetic means. For example, cannabinoids can be isolated by extraction from *Cannabis* plants. Plants in the *Cannabis* genus include, but are not limited to, *Cannabis sativa, Cannabis indica,* and *Cannabis ruderalis.* Each possibility represents a separate embodiment. These plants are the natural sources of cannabinoids. According to some embodiments, certain cannabinoids are isolated or extracted from *Cannabis* plants and then derivatized to the CBDA ester of Formula (I). It is, however, to be understood by the skilled in the art that some of the cannabinoid esters of Formula (I) do not occur in nature, and therefore chemical synthesis is required for their production.

The term "extract" as used herein refers a product prepared by extraction by physical means (e.g. by comminuting, pressing, heating, pulsed electric field assisted treatments, shear treatments and pressure wave treatments), by chemical means (e.g. by treatment with an acid, a base and/or a solvent) and/or by biochemical means. The term refers to a liquid substance obtained through extraction from a given substance, or to a concentrate or essence which is free of, or substantially free of solvent. The term extract may be a single extract obtained from a particular extraction step or series of extraction steps. Extract also may be a combination of extracts obtained from separate extraction steps or separate feedstocks. Such combined extracts are thus also encompassed by the term "extract". Any methods of extraction with suitable solvent are encompassed. Exemplary extraction methods can be found for example in U.S. Pat. No. 6,403,126. The extract may be obtained from any part of the plant e.g. from leaves, flowers, stems, roots, fruits and seeds. The extract may be aqueous or oily.

According to some embodiments, the *Cannabis* plant extract is formed with a suitable solvent or a combination of solvents. According to some embodiments, the solvent is selected from the group consisting of a polar solvent, a hydrocarbon solvent, carbon dioxide, and a combination thereof. According to some embodiments, the *Cannabis* plant extract is produced by a process, which comprises contacting the *Cannabis* plant material with a suitable solvent or a combination of solvents. According to some embodiments, the process further comprises isolating a fraction soluble in said solvent. According to some embodiments, the process further comprises removing the solvent from the soluble fraction, to acquire the extract.

Suitable solvents include but not limited to water, ethanol, ethyl acetate, $CO_2$ (e.g. liquid $CO_2$ or supercritical $CO_2$), methanol, acetone, and acetic acid. Suitable polar solvents include polar organic solvent(s), including, but not limited to halogenated hydrocarbons (e.g. chloroform, dichloromethane), ethers (e.g. diethyl ether, tetrahydrofuran), alcohols (e.g. ethanol, methanol, isopropanol), esters (e.g. ethyl acetate), nitriles (e.g. acetonitrile), sulfones and sulfoxides (e.g. dimethyl sulfoxide, sulfolane), amides (e.g. dimethylformamide) and/or acids (e.g. acetic acid). Each possibility represents a separate embodiment of the invention. Suitable non-polar solvents include hydrocarbons, including but not limited to aliphatic hydrocarbons (e.g. hexane, pentane, heptane, petroleum ether) and/or aromatic hydrocarbons (e.g. benzene, toluene). Each possibility represents a separate embodiment of the invention. According to one embodiment, the solvent is ethanol. According to one embodiment, the solvent comprises ethanol, such as aqueous ethanol. According to another embodiment, the extraction is by $CO_2$. In particular, the term "extract" refers to a liquid or semi-solid or resinous substance obtained through extraction from plants defined in the present application, i.e. extracts obtained from *Cannabis* plant e.g. *Cannabis sativa, Cannabis indica,* and *Cannabis ruderalis.* In some embodiments, the term refers to a mixture of liquid or semi-solid, resinous substances obtained through extraction from two or more different plants. In some embodiments, the term refers also to a compound purified from the extract. According to some embodiments, the term "extract" has the meaning of a mixture or combination of two or more extracts.

The term "*Cannabis* extract" as used herein refers to one or more plant extracts from the *Cannabis* plant. A *Cannabis* extract contains, in addition to one or more cannabinoids, one or more non-cannabinoid components which are co-extracted with the cannabinoids from the plant material. Their respective ranges in weight will vary according to the starting plant material and the extraction methodology used. Cannabinoid-containing plant extracts may be obtained by various means of extraction of *Cannabis* plant material. Such means include but are not limited to supercritical or subcritical extraction with $CO_2$, extraction with hot or cold gas and extraction with solvents. In some embodiments, the term refers to a mixture of liquid or semi-solid, resinous substances obtained through extraction from two or more different *Cannabis* species. In some embodiments, the term refers also to a compound purified from the extract. The term "*Cannabis* plant" as used herein, refers to plants of the genus *Cannabis,* including but not limited to *Cannabis sativa, Cannabis indica,* and *Cannabis ruderalis.* According to some embodiment, *Cannabis* plant is a CBD-rich strain of *Cannabis* plant or THC-rich strain of *Cannabis* plant. Each possibility represents a separate embodiment.

According to some embodiments, the *Cannabis* plant extract is obtained from a species or strain selected from the group consisting of *Cannabis sativa, Cannabis indica, Cannabis ruderalis,* a hybrid strain, a high-CBD strain, a high-THC strain, and a combination thereof. According to some embodiments, the *Cannabis* plant extract comprises at least one cannabinoid selected from the group consisting of CBD, THC, CBN, CBG, CBC, acids thereof and combination thereof.

According to some embodiments, the *Cannabis* plant extract comprises about 1% (w/w) CBD. According to some embodiments, the *Cannabis* plant extract comprises about 10% (w/w) CBD. According to some embodiments, the *Cannabis* plant extract comprises about 25% (w/w) CBD. According to some embodiments, the *Cannabis* plant extract comprises about 45% (w/w) CBD. According to some embodiments, the *Cannabis* plant extract comprises about 1% to about 45% (w/w) CBD, including each value and sub-range within the specified range. According to some embodiments, the *Cannabis* plant extract comprises about 1% to about 10% (w/w) CBD, about 10% to about 25% (w/w) CBD or about 25% to about 40% (w/w) CBD. Each possibility represents a separate embodiment of the invention.

According to some embodiments, the *Cannabis* plant extract comprises about 1% (w/w) THC. According to some embodiments, the *Cannabis* plant extract comprises about 10% (w/w) THC. According to some embodiments, the *Cannabis* plant extract comprises about 25% (w/w) THC. According to some embodiments, the *Cannabis* plant extract comprises about 45% (w/w) THC. According to some embodiments, the *Cannabis* plant extract comprises about 1% to about 45% (w/w) THC, including each value and sub-range within the specified range. According to some embodiments, the *Cannabis* plant extract comprises about 1% to about 10% (w/w) THC, about 10% to about 25% (w/w) THC or about 25% to about 40% (w/w) THC. Each possibility represents a separate embodiment of the invention.

The term "hybrid strain" refers to different strains of *Cannabis,* which include differing amounts and/or ratios of the various cannabinoid compounds. For example, *Cannabis sativa* typically has a relatively high THC/CBD ratio. Conversely, *Cannabis indica* has a relative low THC/CBD ratio compared to *Cannabis sativa* (although the absolute amount of THC can be higher in *Cannabis indica* than in *Cannabis sativa*).

As used herein the terms "high-CBD strain" and "CBD-rich strain" are directed to a strain of *Cannabis plant* which comprises CBD and optionally one or more additional cannabinoids, such as, for example, but not limited to: THC, CBN, and the like. According to some embodiments, CBD is the main component in the high-CBD strain.

As used herein the terms "high-THC strain" and "THC-rich strain" are directed to a strain of *Cannabis* plant which comprises THC and optionally one or more additional cannabinoids, such as, for example, but not limited to: CBD, CBN, and the like. According to some embodiments, THC is the main component in the high-THC strain.

The cannabinoid component combination of the present invention may be generally prepared by conventional methods such as are known in the art of making a mixture with the ratio described above. Such methods typically involve mixing of the CBDA ester and one or more additional cannabinoid compound(s), or one or more extract of a *Cannabis* plant in one or more steps to a relatively uniform state, with or without heating, cooling, application of vacuum, and the like.

Pharmaceutical Compositions

The compositions disclosed herein may be administered locally or systemically.

According to some embodiments, the pharmaceutical composition is formulated for inhalation. According to some embodiments, the pharmaceutical composition is a non-aqueous composition. According to specific embodiments, the pharmaceutical composition is a dry powder formulation. According to some embodiments, the pharmaceutical composition is formulated for an administration via vaporization.

According to some embodiments, the pharmaceutical composition is powder suitable for multi-dose reservoir dry powder inhaler (DPI).

The term "dry powder" as used herein refers to a composition that contains respirable dry particles that are capable of being dispersed in an inhalation device and subsequently inhaled by a subject. Such a dry powder may contain no more than about 25%, no more than about 20%, or no more than about 15% water or other solvent, or be substantially free of water or other solvent, or be anhydrous.

The powders described herein may contain one or more metal cation salts, which can be monovalent metal cation salts, divalent metal cation salts, or combinations thereof. Salts suitable for use in the dry powders include, for example, a sodium salt, a potassium salt, a lithium salt and any combination thereof.

Preferably, the dry particles are highly dispersible, and can be delivered to the respiratory tract of a patient using a passive DPI solely relying on the patient's own breathing pattern. In certain embodiments, the delivery of the respirable dry particles to the respiratory tract is relatively independent of patient's inspiratory flowrate, meaning that the delivered dose is very similar for patients breathing in at a relatively high or low flow rates.

The respirable dry particles described herein can include a physiologically or pharmaceutically acceptable excipient. For example, a pharmaceutically-acceptable excipient includes any of the standard carbohydrates, sugar alcohols, and amino acids that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the therapeutic agent in a manner that adversely affects the desired physiological action. Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins. Representative sugar alcohols include mannitol, sorbitol and the like.

The excipient may be present in an amount less than about 90%, in an amount less than about 80%, in an amount less than about 70%, in an amount less than about 60%, in an amount less than about 50%, in an amount less than about 40%, in an amount less than about 35%, in an amount less than about 30%, in an amount less than about 25%, in an amount less than about 20%, in an amount less than about 17%, in an amount less than about 15%, in an amount less than about 12%, in an amount less than about 10%, in an amount less than about 8%, in an amount less than about 6%, in an amount less than about 5%, in an amount less than about 4%, in an amount less than about 3%, in an amount less than about 2%, or in an amount less than about 1%, all percentages are by weight of the dry particles. Each possibility represents a separate embodiment of the invention.

In some embodiments, the dry particles contain an excipient selected from leucine, maltodextrin, mannitol and any combination thereof. In certain embodiments, the excipient is leucine, maltodextrin, or mannitol. Each possibility represents a separate embodiment of the invention.

According to some embodiments, the pharmaceutical composition is formulated for inhalation, comprising propellant. Pharmaceutically acceptable propellants include inhalation acceptable hydrofluoroalkanes (HFAs). These include, but are not limited to, HFA 134a (tetrafluoroethane) HFA 227 (heptafluoropropane) and mixtures thereof. Each possibility represents a separate embodiment of the invention.

According to some embodiments, the pharmaceutical composition is formed into a dosage form suitable for intranasal, oral, intravenous, intraarterial, transmucosal, or subcutaneous administration. Each possibility represents a separate embodiment of the invention.

According to additional embodiments, the pharmaceutical composition is formulated as a capsule, a tablet, a liquid, or a syrup. Each possibility represents a separate embodiment of the invention. In certain embodiments, the dosage form is granules or pellets delivered in a sachet or filled into capsule or compressed into a tablet.

According to some embodiments, the pharmaceutical composition further comprises triglycerides, fats, lipids, oils, fatty acids, co-solvents or mixtures thereof. Each possibility represents a separate embodiment of the invention. According to certain embodiments, the pharmaceutical composition comprises an edible oil or fat.

According to specific embodiments, the pharmaceutical composition comprises an edible oil selected from the group consisting of copaiba oil, coconut oil, cottonseed oil, soybean oil, safflower oil, sesame oil, sunflower oil, castor oil, corn oil, olive oil, palm oil, peanut oil, and poppy seed oil. Each possibility represents a separate embodiment of the invention. According to specific embodiments, the pharmaceutical composition comprises copaiba oil.

According to some embodiments, the pharmaceutical composition comprises alcohol and a solvent. According to some embodiments, the alcohol is ethanol. According to certain embodiments, the solvent is polyethylene glycol (PEG) or propylene glycol.

According to some embodiments, the pharmaceutical further comprises vitamins, minerals, and/or flavoring agents. Each possibility represents a separate embodiment of the invention.

According to some embodiments, the pharmaceutical composition is formulated for slow release of the cannabinoid component. According to some embodiments, the pharmaceutical composition is formulated for slow release of the CBDA ester. In certain embodiments, the pharmaceutical composition further comprises a release retarding agent or a mixture of release retarding agents. According to some embodiments, the pharmaceutical composition is at least partly coated by an enteric-coating agent.

According to some embodiments, the composition is a gel, wherein the cannabinoid component or acceptable salt thereof is entrapped in a gel matrix. The gel compositions of the present invention may comprise an oil-in water (o/w) emulsion.

Solubilizing and emulsifiers are used to improve the bioavailability of the cannabinoid component. Bioavailability refers to the extent and rate at which the active moiety (drug or metabolite) enters systemic circulation, thereby accessing the site of action.

According to some aspects, within the compositions and methods of the present invention, the bioavailability enhancing agent is an edible oil or fat, a protective colloid, or both a protective colloid and an edible oil or fat. In another aspect, the bioavailability enhancing agent is also a lipophilic active agent taste masking agent. In other aspects, the bioavailability of the lipophilic active agent in a subject is at least about 2 times, 5 times, or 10 times greater than the bioavailability of the lipophilic active agent in the subject in the absence of the bioavailability enhancing agent.

According to some embodiments, the cannabinoid component provided in microencapsulation particles. According to some embodiments, the CBDA ester provided in microencapsulation particles. Encapsulation may result in cannabinoids and other materials present in cannabinoid materials in liposomal capsule particles or other types of particles.

Microencapsulation or nanoencapsulation may increase cannabinoid bioavailability, thereby increasing cannabinoid efficacy after absorption through the mucosal membrane. Microencapsulation or nanoencapsulation may result in particles of 20-40 nm in size. Microencapsulation or nanoencapsulation promotes dissolution of cannabinoid particles in an aqueous environment.

According to some embodiments, the pharmaceutical composition comprises at least one micelle-forming compound selected from the group consisting of a polyoxyethylene ether, ester or alcohol; an alkali metal alkyl sulfate; a bile acid; lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo-cholanylglycine, glycerin, poly glycerin, lysine, polylysine, triolein, salts thereof, and mixtures thereof. Each possibility represents a separate embodiment of the invention. According to certain embodiments, the bile acids or bile acid salts are selected from the group consisting of chenodesoxycholic acid (CDCA), desoxycholic acid (DCA), lithocholic acid (LCA), taurodesoxycholic acid (TDCA), hyodeoxycholic acid (HDCA), taurocholic acid (TCA), glycocholic acid (GCA), and combinations thereof. Each possibility represents a separate embodiment of the invention.

According to some embodiments, the pharmaceutical composition comprises phospholipids. According to certain embodiments, the pharmaceutical composition comprises a phospholipid selected from the group consisting of naturally occurring phospholipids and synthetic phospholipids. According to specific embodiments, the naturally occurring phospholipid is selected from the group consisting of soy lecithin, egg lecithin, hydrogenated soy lecithin, hydrogenated egg lecithin, and a combination thereof. According to certain embodiments, the synthetic phospholipid is selected from the group consisting of phosphocholines, phosphoethanolamines, phosphatidic acids, phosphoglycerols, phosphoserines, mixed chain phospholipids, lysophospholipids, pegylated phospholipids, and a combination thereof. Each possibility represents a separate embodiment of the invention.

According to some embodiments, the phospholipid may form micelles, emulsions or liposomes. Thus, according to some embodiments, the present pharmaceutical composition is in the form of an emulsion, which includes the phospholipid as an emulsifying agent. According to some embodiments, the present pharmaceutical composition is in the form of a micelle, which includes the phospholipid as a micelle-forming agent. According to some embodiments, the present pharmaceutical composition is in the form of a liposomal composition, which includes the phospholipid as the liposome-forming agent.

According to some embodiments, the pharmaceutical composition comprises a cyclodextrin. According to certain embodiments, the cyclodextrin is selected from the group consisting of hydroxypropyl β-cyclodextrin, sulfobutylether β-cyclodextrin, and methyl-β-cyclodextrin (MβCD) and a combination thereof.

According to some embodiments, the pharmaceutical composition comprises a pharmaceutically acceptable solvent, i.e. a non-toxic solvent that is suitable for administration to a mammal with no unacceptable adverse effects. The solvent may be an aqueous or non-aqueous solvent. Suitable solvents include alcohol solutions, especially ethanol.

The pharmaceutical composition may optionally contain a stabilizer and/or a preservative. Phenolic compounds, i.e. compounds comprising one or more hydroxyl groups on a benzyl ring, are particularly suited for this purpose as they not only stabilize the composition, but they also enhance absorption of the composition. Preferred phenolic compounds include phenol, methyl phenol and mixtures thereof.

The pharmaceutical composition may also comprise one or more of the following additional additives: inorganic salts, antioxidants, protease inhibitors, colorants and flavoring agents. Non-limiting examples of inorganic salts include sodium, potassium, calcium and zinc salts, especially sodium chloride, potassium chloride, calcium chloride, zinc chloride and sodium bicarbonate.

Orally administered formulations such as tablets may optionally be coated and may be formulated so as to provide sustained, delayed or controlled release of the active ingredient therein.

The term "sustained" as used herein refers to a composition which provides prolonged, long or extended release of the therapeutic agent. This term may further refer to a composition which provides prolonged, long or extended duration of action (pharmacokinetics) of a pharmaceutical composition comprising a therapeutically effective amount of the pharmaceutical composition of the present invention.

The pharmaceutical composition can include additional ingredients including but not limited to the excipients described herein. According to certain embodiments, one or more therapeutic agents of the dosage unit may exist in an extended or control release formulation and additional therapeutic agents may not exist in extended-release formulation. For example, the cannabinoid component ester described herein may exist in a controlled release formulation or extended-release formulation in the same dosage unit with another agent that may or may not be in either a controlled release or extended-release formulation. Thus, in certain embodiments, it may be desirable to provide for the immediate release of one or more of the agents described herein, and the controlled release of one or more other agents.

According to some embodiments, the composition further comprises at least one pharmaceutically acceptable excipient. According to additional embodiments, the excipient is selected from the group consisting of emulsifiers, buffering agents, pH adjusting agents, tonicity modifiers, preservatives, antioxidants, stabilizers, and a combination thereof.

According to some embodiments, the pharmaceutically acceptable carrier is an aqueous carrier. In some embodiments the aqueous carrier is a physiologically acceptable buffer having physiological or near-physiological pH.

According to some embodiments, the composition further comprising at least one pharmaceutically acceptable excipient. According to further embodiments, the excipient is selected from, but not limited to, emulsifiers, buffering agents, pH adjusting agents, tonicity modifiers, preservatives, antioxidants, stabilizers, or any other pharmaceutically acceptable excipient known in the art.

The pharmaceutical composition may comprise at least one physiologically acceptable film forming agent such as pullulan, methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylamides, polyalkylene oxides, carrageenan, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, alginic acid, pea starch, dextrin, pectin, chitin, chitosan, levan, elsinan and mixtures thereof. Additional film forming agents may be added to optimize characteristics such as tensile strength, stability, flexibility and brittleness including agents such xanthan gum, tragacanth gum, guar gum, locust bean gum, acacia gum, arabic gum, collagen, gelatin, zein, gluten, soy protein isolate, whey protein isolate, casein and mixtures thereof.

According to some embodiment, the orally administrable formulation comprises a mixture of sodium carboxymethylcellulose and hydroxypropyl-cellulose or methyl cellulose as the film-forming agents. The ratio of sodium carboxymethylcellulose to hydroxypropyl cellulose (or methylcellulose) used to make the formulation is chosen to yield the desired dissolution time and to further impart acceptable product handling characteristics.

According to some embodiments, the composition comprises less than about 10% (w/w) of the cannabinoid component. According to additional embodiments, the composition comprises less than about 7% (w/w) of the cannabinoid component. According to further embodiments, the composition comprises less than about 5% (w/w) of the cannabinoid component. According to yet further embodiments, the composition comprises less than about 2% (w/w) of the cannabinoid component. According to some embodiments, the composition comprises less than about 1% (w/w) of the cannabinoid component. According to additional embodiments, the composition comprises less than about 0.5% (w/w) of the cannabinoid component. It is to be understood that the w/w unit is intended to refer to the relative weight amount of the cannabinoid component within the composition. For example, if the total weight of the composition is 1 gram and the weight of the cannabinoid component therein is 50 milligrams, the composition is said to comprise 5% (w/w) of the cannabinoid component.

According to some embodiments, the pharmaceutical composition is in a solid or semisolid form. The term "semisolid" refers to a form which on one hand supports its own weight and holds its shape and on the other hand is capable of conforming in shape in response to external pressure.

The invention also provides a pharmaceutical pack or kit comprising one or more containers filled with one or more of the pharmaceutical compositions of the invention.

It shall be understood that the amount of any active agent that is administered to a patient to treat that patient, will be administered in a therapeutically effective amount, as determined by ordinarily skilled physicians, pharmacologists, and toxicologists that take into account the weight and age of the patient. In any event, where the drug has been approved by a regulatory authority (e.g., the U.S. Food and Drug Administration), a therapeutically effective amount of the cannabinoid component is an amount approved by the regulatory authority.

According to some embodiments, the pharmaceutical composition further comprises an additional therapeutic agent.

Methods of Preparation

The compositions of the present invention may be formulated for an inhalation as known in the art. In such a formulation, CBDA-ME is prepared in some embodiments as an inhalable dry powder or as an aerosol solution. Dry powder formulations for inhalation therapy are described, e.g., in U.S. Pat. No. 10,588,870 to Lipp and Sung; U.S. Pat. No. 5,993,805 to Sutton et al.; U.S. Pat. No. 6,921,527 to Platz et al.; WO 1999016419 to Tarara et al.; and WO 2000000215 to Bot et al.

The compositions of the present invention may be formulated as single-phase aqueous, emulsion or multiple emulsions. According to some embodiments, the composition is formulated as emulsion. These emulsions may be oil-in-water (o/w) (including silicone in water) emulsions, water-in-oil (including water-in-silicone) (w/o) emulsions, or multiple emulsions such as oil-in-water-in-oil (o/w/o) or water-in-oil-in-water (w/o/w). It is understood that the oil phase can comprise silicone oils, non-silicone organic oils, or mixtures thereof. The compositions can comprise two immiscible phases that are admixed at the time of use by shaking. Each possibility represents a separate embodiment of the present invention.

According to some embodiments, the composition is made by preparing a dispersion of each component in a suitable solvent (dispersant), adjusting the dispersion pH with a pH adjusting agent, if necessary, and admixing the dispersions with shear to permit the formation of the desired matrix.

A common mode of administration of medical *Cannabis* is by dissolving the *Cannabis* extract or pure cannabinoid in triglyceride oils, such as vegetable oils, for oral delivery. The oil is either filled into capsules or used as-is in various volumes. In contrast to inhalation, the oral route of drug administration is most convenient to most people, and is perceived as an acceptable mode of self-medication, such as consuming a pill. In such cases, an immediate release of the cannabinoids is obtained with fast absorption and an intermediate duration time of activity, but longer than smoking or vaporizing. A major drawback of dissolving cannabinoids in triglyceride oils is the inability to reach high concentrations of cannabinoids in a single unit dose, due to the limited solubility of cannabinoids and specifically CBD in vegetable oils. Therefore, many products are "*Cannabis* oils" which are cannabinoids dissolved in a vegetable oil and administered in relatively large volumes. However, a limitation of this approach is the unfavorable taste and smell, characteristic of the vegetable oils and cannabinoids, which often result in poor patient compliance.

A person skilled in the art can select the appropriate presentation form, and the method of preparing it on the basis of general knowledge, taking into account the nature of the constituents used and the intended use of the composition. Kits containing the above compositions are also contemplated. Compositions of the present invention can be packaged to contain, separately or in kit form together with a container, instructions or instruction brochure.

Methods of Use

According to an aspect, the present invention provides a method for treating PWS, comprising administering to a subject in need thereof a therapeutically effective amount of a pharmaceutical composition comprising a cannabinoid component, wherein the cannabinoid component comprises a CBDA ester represented by the structure of Formula (I) alone or in combination with one or more additional cannabinoid compound(s), and a pharmaceutically acceptable carrier, excipient or diluent, Formula (I)

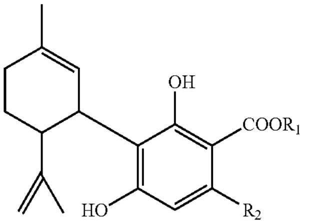

wherein $R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

According to an additional aspect, the present invention provides a method for treating Prader-Willi Syndrome, comprising administering to a subject in need thereof a therapeutically effective amount of a pharmaceutical composition comprising a cannabinoid component, wherein the cannabinoid component comprises a CBDA ester represented by the structure of Formula (I) alone or in combination with one or more additional cannabinoid compound(s), and a pharmaceutically acceptable carrier, excipient or diluent, Formula (I)

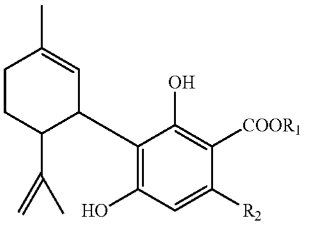

wherein $R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

In certain embodiments the one or more additional cannabinoid compound(s) are present in one or more extracts of a *Cannabis* plant.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term “effective amount” refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy. For example, a “therapeutically effective amount” of the CBDA ester refers to an amount that is effective for preventing, ameliorating, or treating the specified disease or disorder. Similarly, a “therapeutically effective amount” of a combination of the CBDA ester and a second compound refers to an amount of CBDA ester and an amount of the second compound that, in combination, is effective for ameliorating, or treating the specified disease or disorder.

The term “treatment” or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

As used herein, the term “subject” designates a mammal, preferably a human.

In some embodiments, the pharmaceutical composition described herein is for use in treating PWS. According to certain embodiments, the pharmaceutical composition described herein is for use in treating or ameliorating at least one symptom associated with PWS.

According to some embodiments, the pharmaceutical composition is used in combination with other therapeutic agents for treatment of PWS.

The beneficial effect can be evidenced, for example, by a delayed onset of clinical symptoms of the disease or condition in a susceptible subject, a reduction in severity of some or all clinical symptoms of the disease or condition, a slower progression of the disease or condition, a reduction in the number of relapses of the disease or condition, an improvement in the overall health or well-being of the subject, by other parameters well known in the art that are specific to the particular disease or condition, and combinations of such factors.

The route of administration can be by any route and will be determined based on the physician and the patient. All other routes of administration of a therapeutically effective amount of an agent to treat a patient having treating PWS are contemplated herein and include, without limitation, enteral (e.g., orally), or parenteral (e.g., intravenous, subcutaneous or by inhalation), or other routes (e.g., intranasal, intradermal, subcutaneous, and transdermal).

According to some embodiments, the pharmaceutical composition is administered by inhalation. According to certain embodiments, the pharmaceutical composition is administered intranasally. According to other embodiments, the pharmaceutical composition is administered orally.

According to some embodiments, the pharmaceutical composition is administered twice a day, three times a day or more. According to some embodiments, the pharmaceutical composition is administered once a day, twice a week, once a week, once in two weeks, once in three weeks or once a month. According to yet further embodiments, the composition is administered once in two months, once in three months, once in four months, once in five months or once in six months.

According to some embodiments, the pharmaceutical composition is administered for a period of greater than a week. According to some embodiments, the pharmaceutical composition is administered for a period of greater than four weeks. According to some embodiments, the pharmaceutical composition is administered for a period of greater than two months. According to some embodiments, the pharmaceutical composition is administered for a period of greater than 3, 4, 5, or 6 months.

According to some embodiments, the effective dose of the cannabinoid component ranges from 0.1 to 500 mg/kg/day of body weight, from 1 to 250 mg/kg/day of body weight, from 2 to 100 mg/kg/day of body weight, or from 5 to 30 mg/kg/day, and may be in single dose or divided throughout the day. Each possibility represents a separate embodiment of the invention.

According to some embodiments, the effective dose of the CBDA ester ranges from 0.1 to 500 mg/kg/day of body weight, from 1 to 250 mg/kg/day of body weight, from 2 to 100 mg/kg/day of body weight, or from 5 to 30 mg/kg/day, and may be in single dose or divided throughout the day. Each possibility represents a separate embodiment of the invention.

According to some embodiments, the effective dose of CBDA-ME ranges from 0.1 to 500 mg/kg/day of body weight, from 1 to 250 mg/kg/day of body weight, from 2 to 100 mg/kg/day of body weight, or from 5 to 30 mg/kg/day, and may be in single dose or divided throughout the day. Each possibility represents a separate embodiment of the invention.

According other embodiments, the pharmaceutical composition is administered at a unit dosage form of approximately 0.05 g/kg/day to approximately 0.5 g/kg/day.

The active agents of the present invention are effective over a wide dosage range. According to certain embodiments, the cannabinoid component dosage is 0.5 mg, 1 mg, 2 mg, 3 mg, 5 mg, 10 mg, 15 mg, 20 mg, 25, mg, 50 mg, 75 mg, 100 mg, 200 mg, 300 mg, 400 mg, 500 mg, 600 mg, 700 mg, 800 mg, 900 mg, 1000 mg, 1500 mg, 2000 mg, 3000 mg, 4000 mg, 5000 mg, 6000 mg, 7000 mg, 8000 mg, 9000 mg, or 10000 mg per day orally. According to certain embodiments, the CBDA ester dosage is about 0.5 mg, 1 mg, 2 mg, 3 mg, 5 mg, 10 mg, 15 mg, 20 mg, 25, mg, 50 mg, 75 mg, 100 mg, 200 mg, 300 mg, 400 mg, 500 mg, 1000 mg, 5000 mg, or 10000 mg per day orally. According to certain embodiments, CBDA-ME dosage is about 0.5 mg, 1 mg, 2 mg, 3 mg, 5 mg, 10 mg, 15 mg, 20 mg, 25, mg, 50 mg, 75 mg, 100 mg, 200 mg, 300 mg, 400 mg, 500 mg, 1000 mg, 2000 mg, 5000 mg, or 10000 mg per day orally.

According to some embodiments, the unit dosage form is administered with food at any time of the day, without food at any time of the day, with food after an overnight fast (e.g., with breakfast).

It is conceived that in some embodiments the therapeutic methods according to the invention may involve combination therapies. In other words, that the compositions of the invention may be administered in combination with one or more additional compounds or therapies, the latter using enteral or parenteral and include, but are not limited to, by inhalation, oral, intradermal, intramuscular, intravenous, subcutaneous, intranasal, and transdermal administration routes.

The following examples describe specific aspects of the invention to illustrate the invention and provide a description of the present methods for those skilled in the art. It should be noted that the term “and” or the term “or” is generally employed in its sense including “and/or” unless the content clearly dictates otherwise. As used herein, the term "about", when referring to a measurable value such as an amount, a temporal duration, and the like, is meant to encompass variations of ±10%, more preferably ±5%, even more preferably ±1%, and still more preferably ±0.1% from the specified value, as such variations are appropriate to perform the disclosed methods.

The Examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

EXAMPLES

Example 1. Synthesis of Cannabidiolic Acid (CBDA)

The preparation process described in the PCT application WO 2018/235079 was applied. A mixture of Cannabidiol (CBD, 314 mg, 1 mmol) and 2 molar solution of Magnesium Methyl Carbonate (MMC/2M, 1.5 ml, 3 mmol) in dimethylformamide (DMF) was heated at 130° C. for 3 hours. Then the reaction was cooled to 0° C., acidified with 10% hydrochloric acid and extracted with ether. The organic layer was washed with saline, dried over the drying agent magnesium sulfate ($MgSO_4$) and then evaporated. The crude compound was then cleaned by column chromatography (20% ether-petroleum ether).

Example 2. Synthesis of Cannabidiolic Acid Methyl Ester (CBDA-ME)

The preparation process described in the PCT application WO 2018/235079 was applied. To a solution of Cannabidiolic Acid (CBDA) (175 mg, 0.488 mmol) in 2.5 ml dichloromethane ($CH_2Cl_2$), was added 0.02 ml of methanol ($CH_3OH$, 0.488 mmol) and 7.2 mg of 4-Pyrrolidinopyridine (0.048 mmol). The reaction was stirred for 5 minutes at room temperature followed by the addition of the coupling agent, N,N' Dicyclohexylcarbodiimide (DCC) (121 mg, 0.585 mmol) and stirred overnight. Then the solvent was evaporated and the crude mixture acidified with 5% hydrochloric acid and extracted with dichloromethane ($CH_2Cl_2$). The organic layer was washed with saturated aqueous sodium bicarbonate ($NaHCO_3$), dried over the drying agent magnesium sulfate ($MgSO_4$) and then evaporated. The crude compound is then cleaned by column chromatography (2% ether-petroleum ether).

$^1$H-NMR spectra were obtained using a Bruker AMX 300 MHz apparatus using the deuterated DMSO. Thin-layer chromatography (TLC) was run on silica gel 60F254 plates (Merck). Column chromatography was performed on silica gel 60 Å (Merck). Compounds were located using a UV lamp at 254 nm.

$^1$H NMR (300 MHz, (($CD_3)_2SO$)) δ 6.18 (1H, s, Ar), 5.07 (1H, s), 4.44 (1H, s), 4.41 (1H, s), 3.82 (3H, s), 3.35 (1H, m), 2.66 (1H, m), 2.49 (2H, t), 2.09 (1H, b), 1.95 (3H, s), 1.71-1.05 (12, ms), 0.86 (3H, t).

Example 3. The Therapeutic Effect of CBDA-ME in a Prader-Willi Syndrome Model A Magel2-null mice model of Prader-Willi Syndrome was used to examine the effects of CBDA-ME treatment.

Study Design

The experimental protocol used was approved by the Institutional Animal Care and Use Committee of the Hebrew University, Israel, which is an AAALAC International accredited institute. Male 6-week-old Magel2$^{null}$ mice and their wild-type littermate controls were maintained under a 12-h light/dark cycle and fed ad libitum. To generate diet-induced obesity, the mice were fed either a high-fat diet (HFD) (60% of calories from fat, 20% from protein, and 20% from carbohydrates; Research Diet, D12492) or a standard laboratory diet (STD, 14% fat, 24% protein, 62% carbohydrates; NIH-31 rodent diet) for 14-16 weeks. Then, HFD-fed obese mice received vehicle (1% Tween80, 4% DMSO, 95% Saline) or CBDA-ME (20 or 40 mg/kg) daily for 28 days by intraperitoneal (ip) injections. Age-matched control mice on STD received vehicle daily.

Description of Test System:

Body weight was monitored daily. Total body fat and lean masses were determined by EchoMRI-100H™ (Echo Medical Systems LLC, Houston, TX, USA). At weeks 20-22, the mice were euthanized by a cervical dislocation under deep anesthesia. The brain, kidneys, liver, fat pads, pancreas and muscles were removed, and the liver and kidney were also weighed. The samples were either snap-frozen or fixed in buffered 4% formalin. Trunk blood was collected for determining the biochemical parameters.

Methods:

Multi-parameter metabolic assessment—Metabolic profile of the mice was assessed by using the Promethion High-Definition Behavioral Phenotyping System (Sable Instruments, Inc., Las Vegas, NV, USA). Data acquisition and instrument control were performed using MetaScreen software version 2.2.18.0, and the obtained raw data were processed using ExpeData version 1.8.4 using an analysis script detailing all aspects of data transformation. Mice with free access to food and water (which were continuously measured) were subjected to a standard 12 h light/12 h dark cycle, which consisted of a 24 h acclimation period followed by 24 h of sampling. Respiratory gases were measured by using the GA-3 gas analyzer (Sable Systems, Inc., Las Vegas, NV, USA) using a pull-mode, negative-pressure system. Air flow was measured and controlled by FR-8 (Sable Systems, Inc., Las Vegas, NV, USA), with a set flow rate of 2000 mL/min. Water vapor was continuously measured and its dilution effect on $O_2$ and $CO_2$ was mathematically compensated. Effective body mass was calculated by ANCOVA. Fat oxidation (FO) and carbohydrate oxidation (CHO) were calculated as $FO=1.69\times VO_2-1.69\times VCO_2$ and $CHO=4.57\times VCO_2-3.23\times VO_2$ and expressed as g/d/kg$^{eff.Mass}$.

Locomotor activity—Locomotor activity, voluntary activity and running wheel capability were quantified by the number of disruptions of infrared XYZ beam arrays with a beam spacing of 0.25 cm in the Promethion High-Definition Behavioral Phenotyping System (Sable Instruments, Inc., Las Vegas, NV, USA).

Glucose tolerance test (ipGTT) and insulin tolerance test (ipITT)-Mice that fasted overnight were injected with glucose (1.5 g/kg, ip), followed by a tail blood collection at 0, 15, 30, 45, 60, 90, and 120 minutes. Blood glucose levels were determined using the Contour glucometer (Bayer, Pittsburgh, PA). The following day, mice underwent fasting for 6 h before receiving insulin (0.75 U/kg, ip; Eli Lilly), and blood glucose levels were determined at the same intervals as above.

Blood biochemistry—Serum levels of cholesterol, triglycerides (TG), high-density lipoprotein (HDL), low-density lipoprotein (LDL), glucose, alanine aminotransferase (ALT), aspartate aminotransferase (AST), and alkaline phosphatase (ALP) were determined using the Cobas C-111 chemistry analyzer (Roche, Switzerland). Fasting blood glucose was measured using the Contour glucometer.

Hepatic lipid content—Liver tissues were extracted and their triglyceride and cholesterol contents were determined using the Cobas C-111 chemistry analyzer (Roche, Switzerland) or the EnzyChrom™ Triglyceride assay kit (BioAssay Systems, Hayward CA, USA).

Histopathology—First, 5 μm paraffin-embedded liver sections from 5 animals per group were stained with hematoxylin-eosin staining. Liver images were captured with a Zeiss AxioCam ICc5 color camera (Carl Zeiss AG, Jena, Germany) mounted on a Zeiss Axio Scope.A1 light microscope (Carl Zeiss AG, Jena, Germany) and taken from 10 random 40× fields of each animal.

Statistical Methods—Results in multiple groups and time-dependent variables were compared by ANOVA followed by Tukey post-hoc test. Significance was set at $P<0.05$ using the following signs: *$P<0.05$ relative to STD-Veh; #$P<0.05$ relative to HFD-Veh; ^$P<0.05$ relative to HFD-20 mg/kg of CBDA-ME.

Figure 1F:
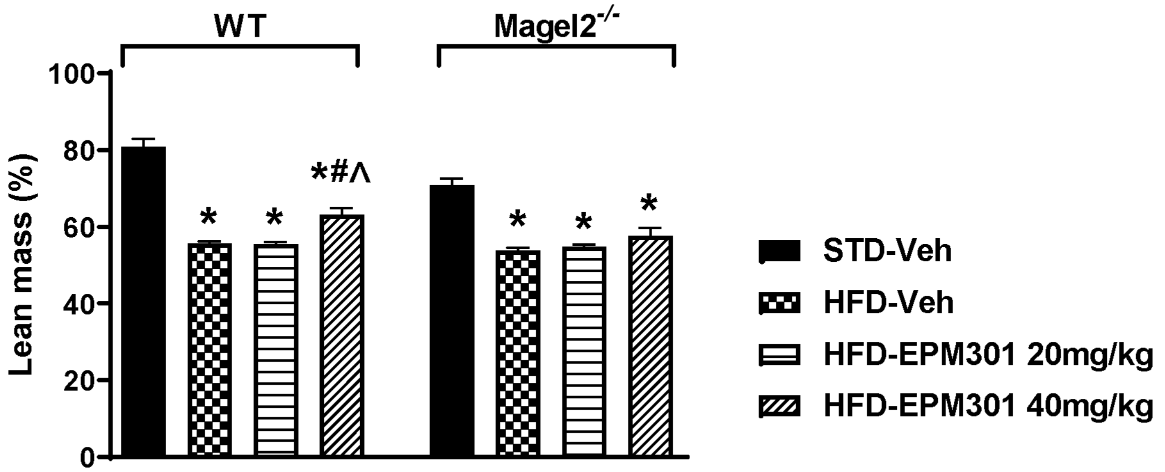

Results:

The metabolic profile of CBDA-ME was examined in mice with diet-and genetic-induced obesity (DIO, GIO). Male Magel2$^{null}$ mice and their wild-type littermate controls fed a high-fat diet (HFD) for 14-16 weeks became obese and then started treatment with daily ip injections of vehicle, or CBDA-ME (20 mg/kg/d or 40 mg/kg/d) for 28 days. Age- and sex-matched mice on STD served as controls. The overweight and increased adiposity of Magel2$^{null}$ mice on HFD were reduced by CBDA-ME in both doses; however, in WT mice these effects were only observed in the higher dose of 40 mg/kg (FIG. 1A-1E). 40 mg/kg-treated WT mice were also the only group that showed a significant increase in lean body mass percentage (FIG. 1F).

Figure 2A:
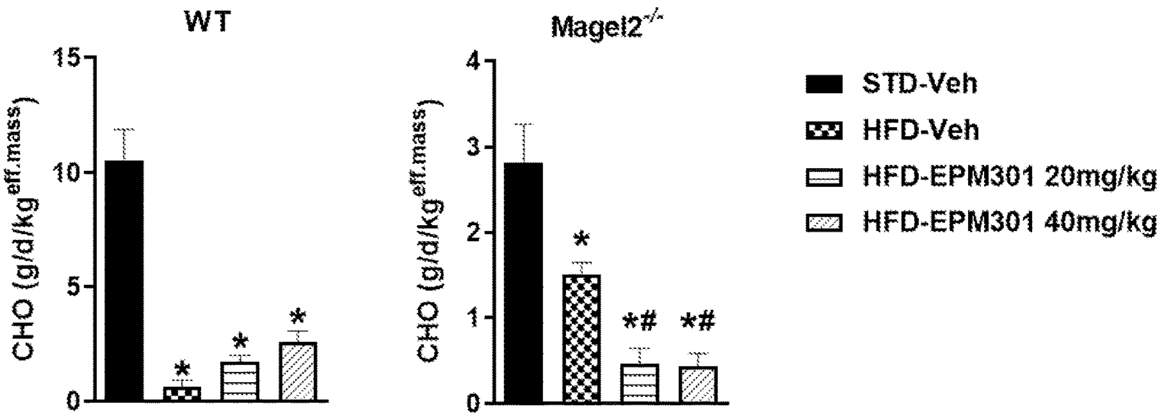
FIGS. 2A-2B show the effect of CBDA-ME on carbohydrate oxidation (FIG. 2A) and fat oxidation (FIG. 2B) in WT or PWS mouse model fed with high-fat diet (HFD).
Figure 2B:
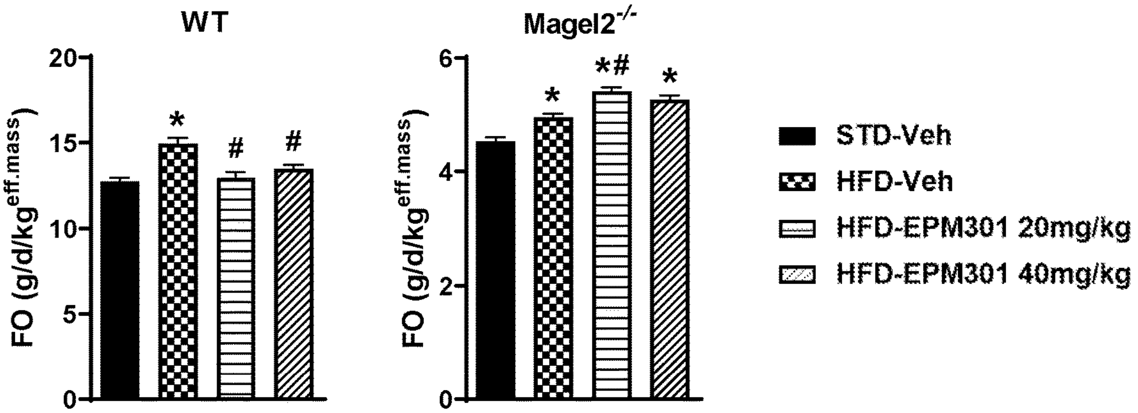
Figure 3A:
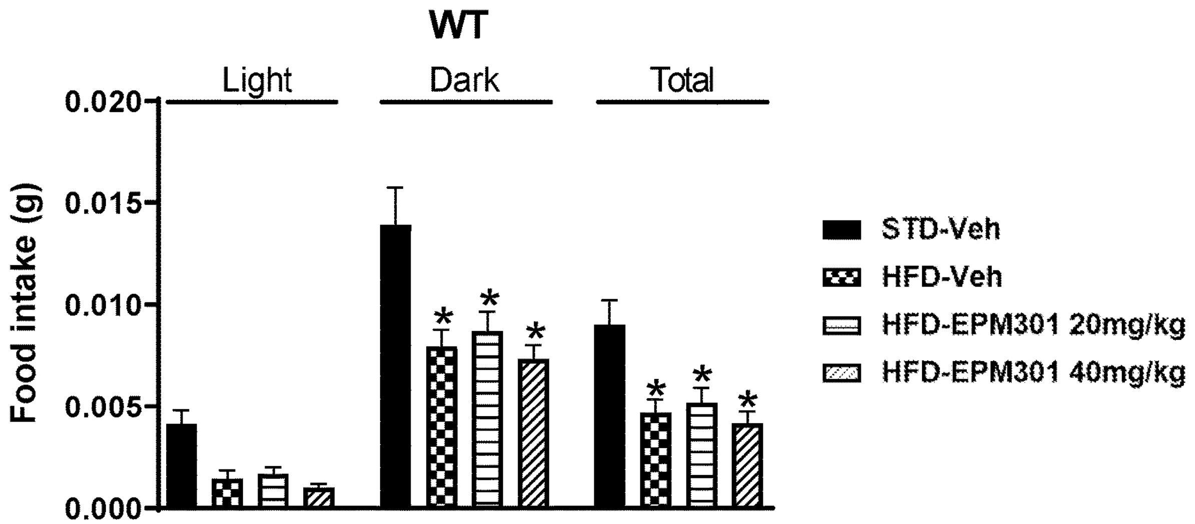
FIGS. 3A-3C show the effect of CBDA-ME on food intake in WT or PWS mouse model fed with high-fat diet (HFD).
Figure 3B:
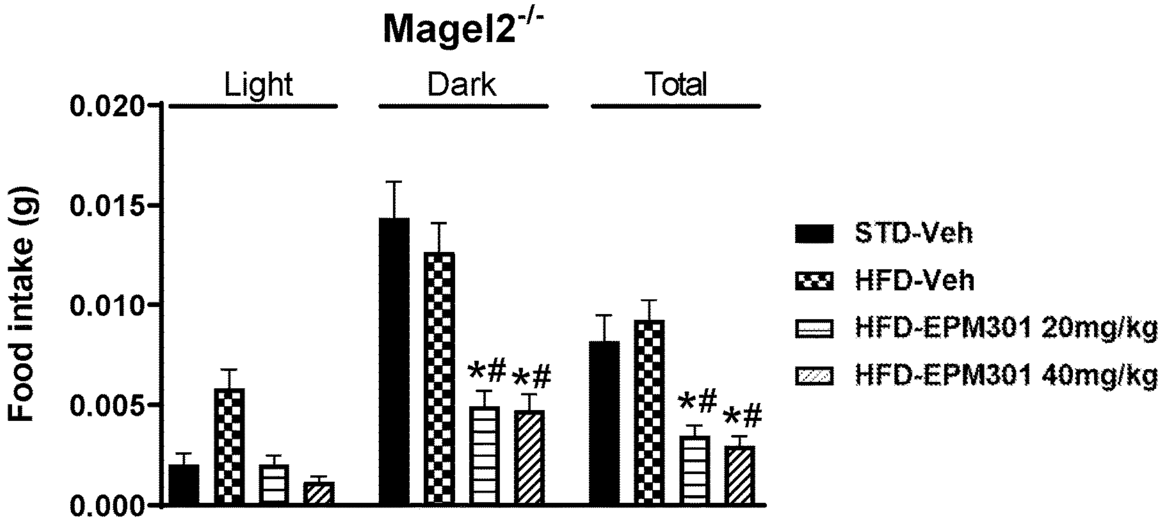
Figure 3C:
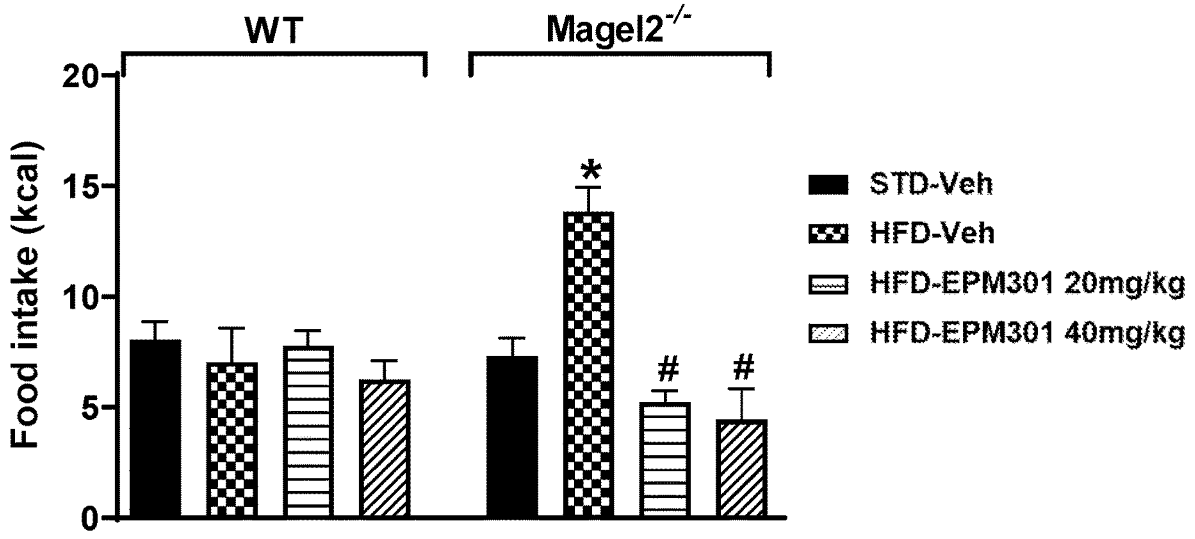

Changes in the metabolic profile of the mice treated with CBDA-ME were demonstrated using an indirect calorimetry assessment. As shown in FIG. 2A-2B, CBDA-ME downregulated the utilization of fat and upregulated carbohydrate oxidation in WT mice. In comparison, Magel2$^{null}$ mice showed an opposite effect by further upregulating fat oxidation and downregulating carbohydrate oxidation. These metabolic differences were associated with the ability of CBDA-ME to inhibit food intake and hyperphagia only in Magel2$^{null}$ mice, an effect that was not observed in their WT littermate controls (FIG. 3).

Figure 4:
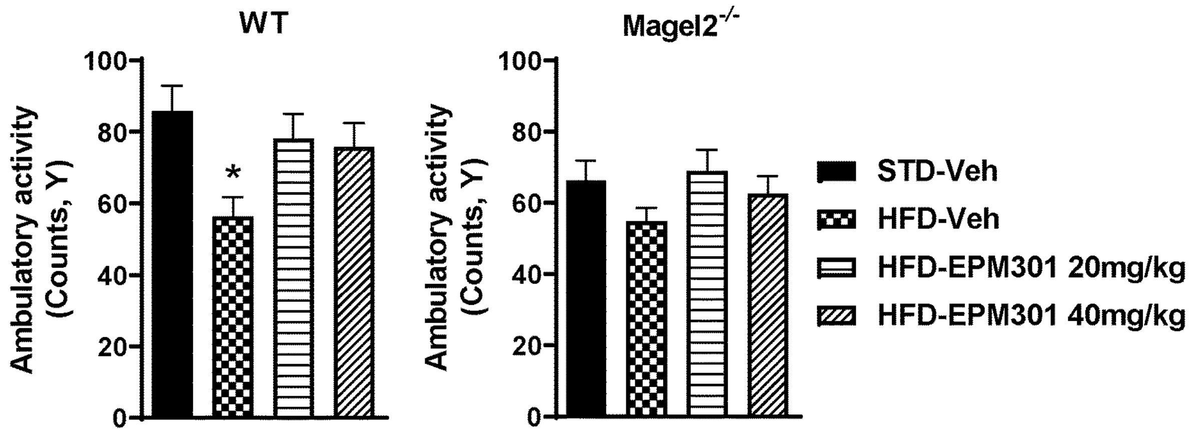
FIG. 4 shows the effect of CBDA-ME on ambulatory activity in WT or PWS mouse model fed with high-fat diet (HFD).

CBDA-ME restored the reduced ambulatory activity in both WT and Magel2$^{null}$ mice (FIG. 4).

Figure 5A:
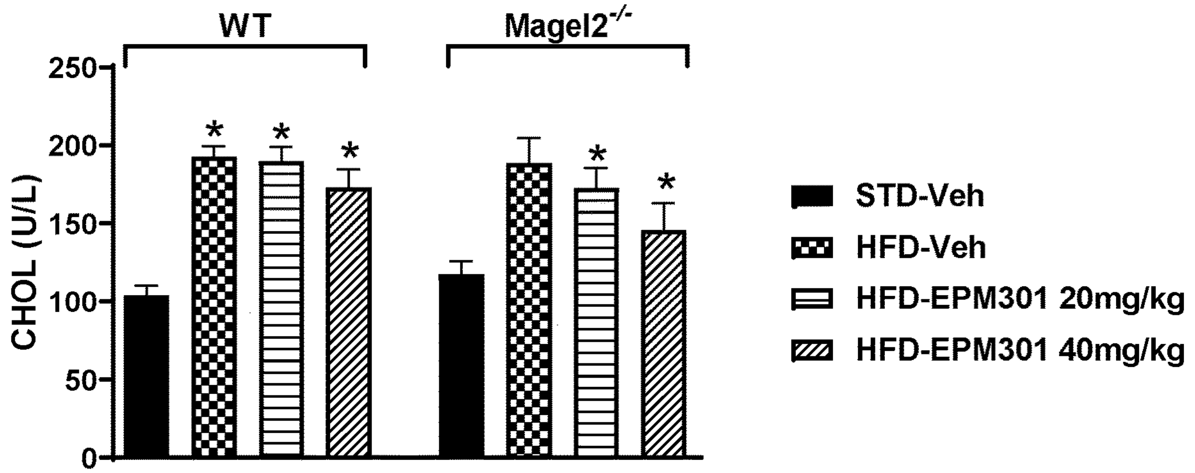
FIGS. 5A-5D show the effect of CBDA-ME on lipid profile in WT or PWS mouse model fed with high-fat diet (HFD).
Figure 5B:
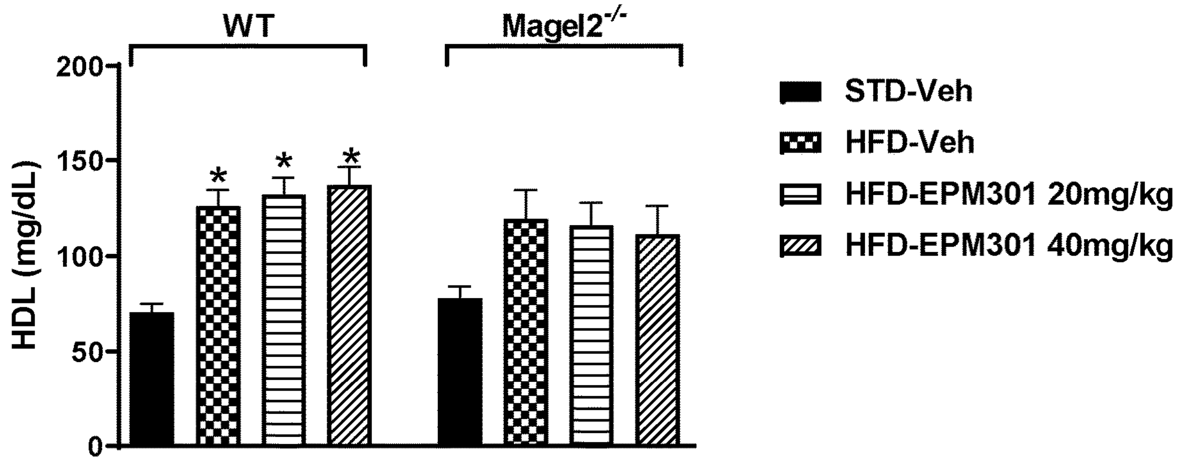
Figure 5C:
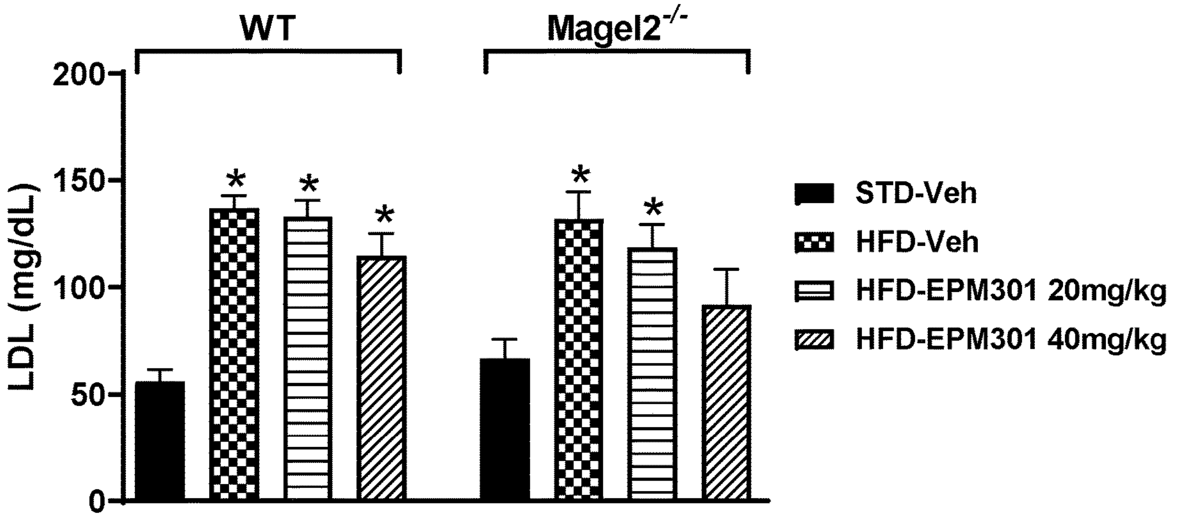
Figure 5D:
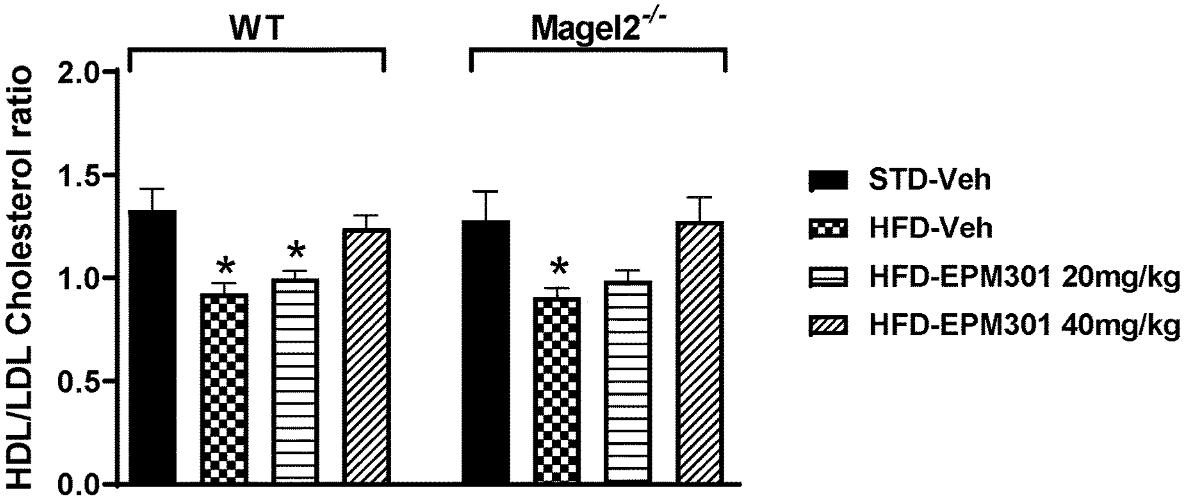

The reduction in body weight in DIO mice treated with CBDA-ME resulted in some improvement in lipid profile, in which the HFD-induced hypercholesterolemia was reduced (FIG. 5A). CBDA-ME had no effect on serum HDL, which remained high (FIG. 5B). Still, CBDA-ME reduced the levels of serum LDL (FIG. 5C), which contributed to increased ratio between HDL-to-LDL (FIG. 5D). These effects on lipid profile were more prominent in the mice treated with the higher dose of CBDA-ME.

Figure 6A:
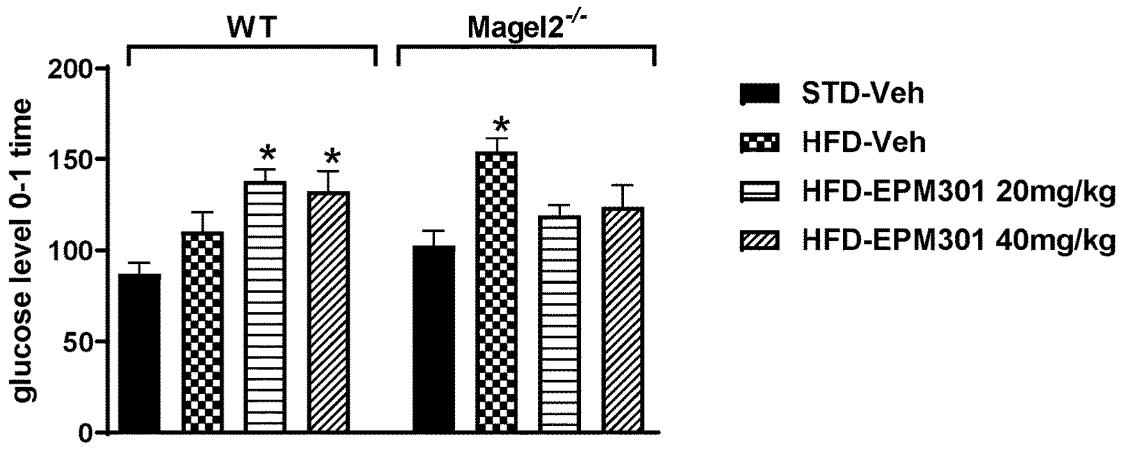
FIGS. 6A-6F show the effect of chronic treatment of CBDA-ME on blood glucose levels (FIG. 6A), glucose tolerance and insulin sensitivity (FIG. 6B-F) in WT or PWS mouse model fed with high-fat diet (HFD).
Figure 6B:
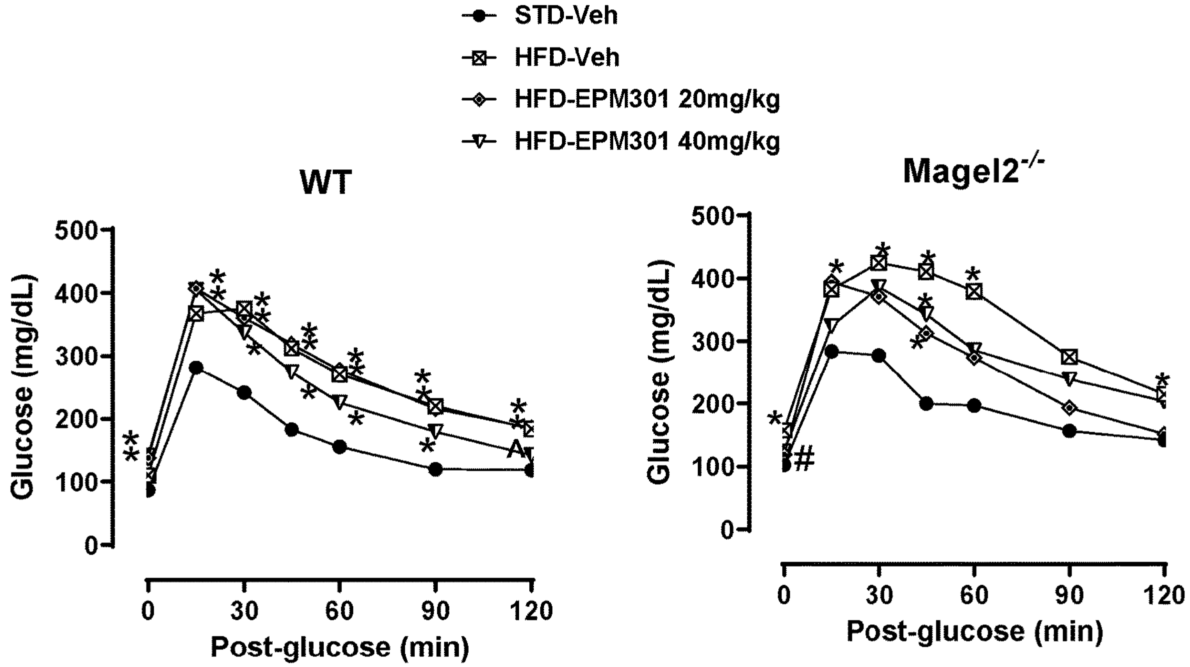
Figure 6C:
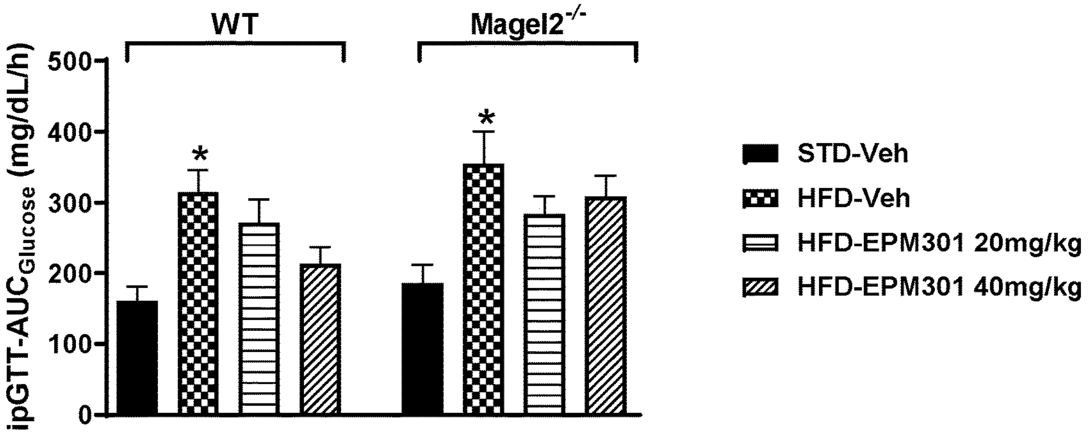
Figure 6D:
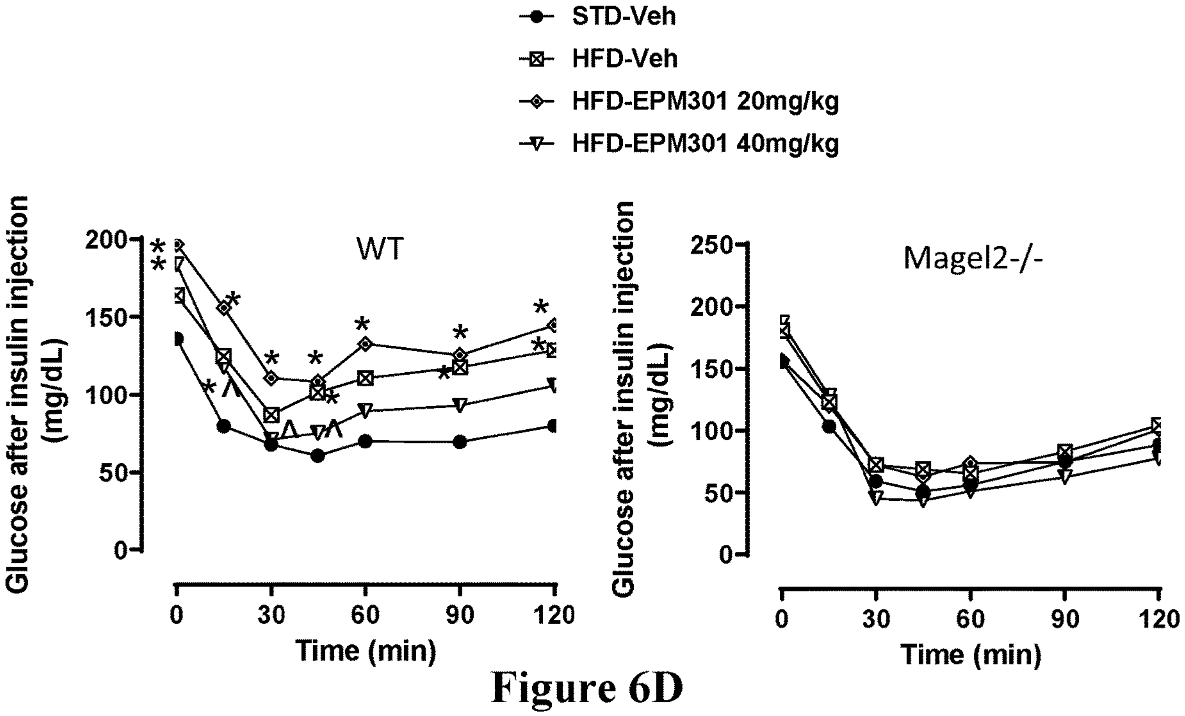
Figure 6E:
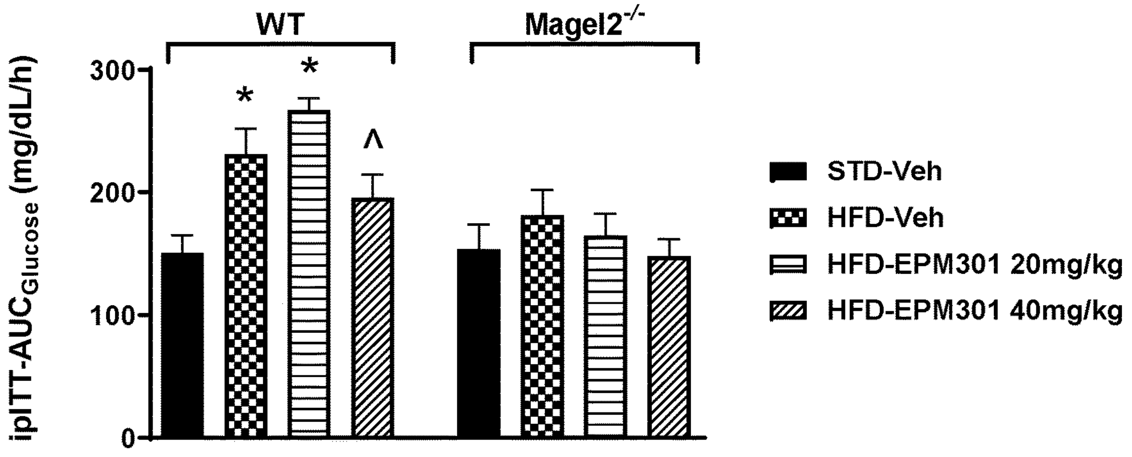
Figure 6F:
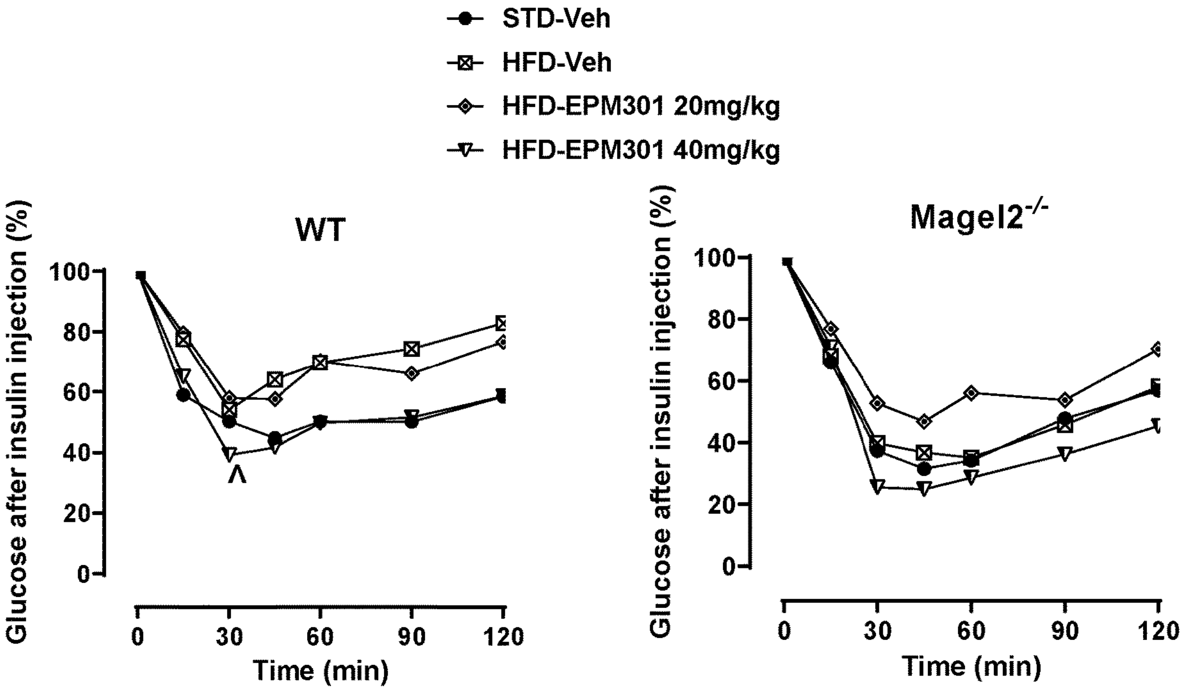

Chronic treatment with EPM301 reduced the fasting blood glucose levels only in Magel2$^{null}$ mice (FIG. 6A). Still, both WT and Magel2$^{null}$ mice treated with CBDA-ME demonstrated reduction in the obesity-induced glucose intolerance. Whereas this effect was observed in WT mice treated with EPM301 in a dose of 40 mg/kg, CBDA-ME was found effective in Magel2$^{null}$ mice in both doses tested (FIG. 6B, 6C). Insulin sensitivity was slightly improved in both genotypes under 40 mg/kg CBDA-ME (FIG. 6D-6F).

Figure 7A:
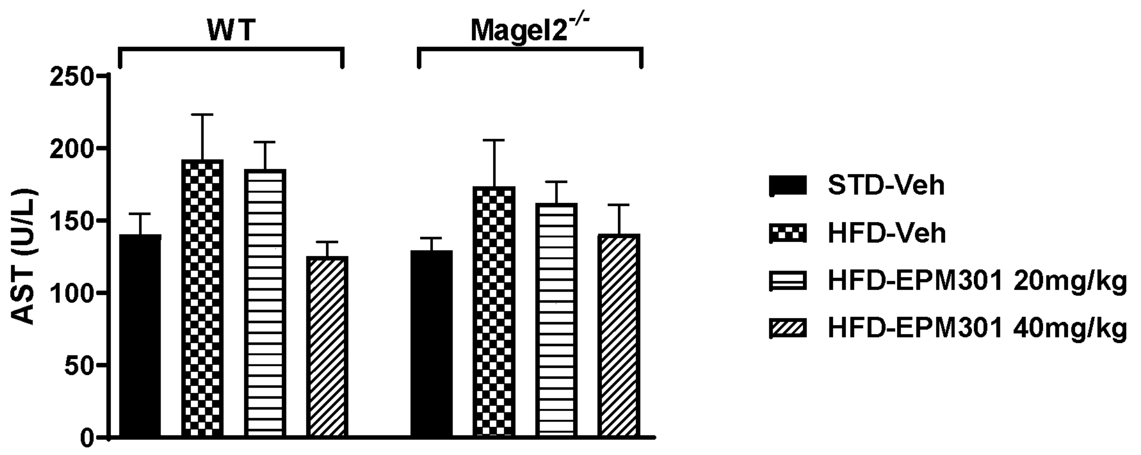
FIGS. 7A-7C show the effect of CBDA-ME on alanine transaminase (ALT), aspartate transaminase (AST), and alkaline phosphatase (ALP) in WT or PWS mouse model fed with high-fat diet (HFD).
Figure 7B:
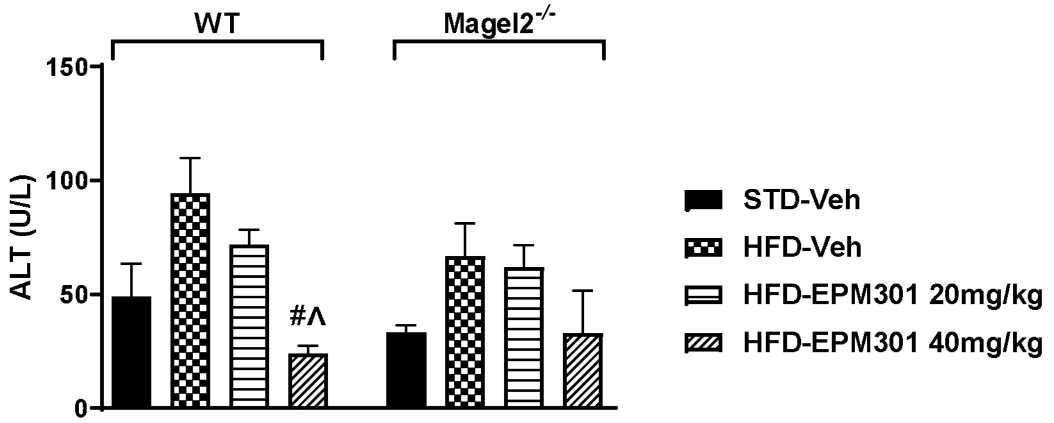
Figure 7C:
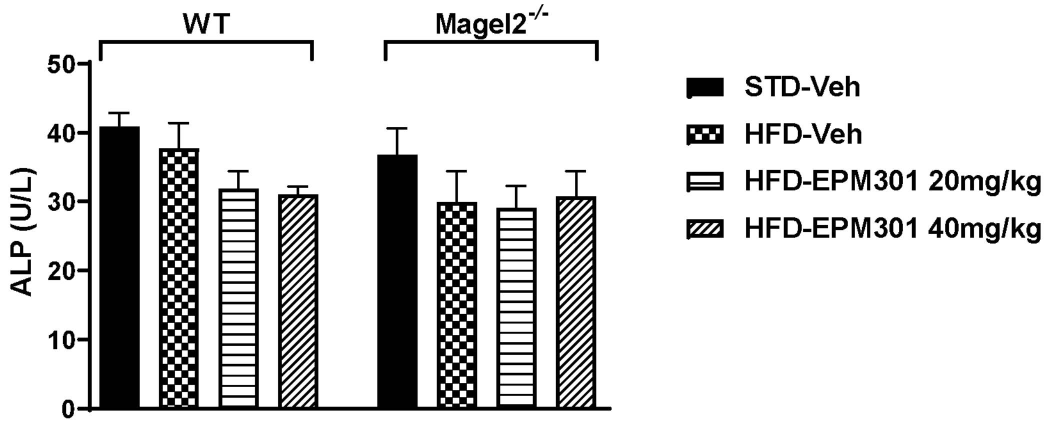
Figure 8A:
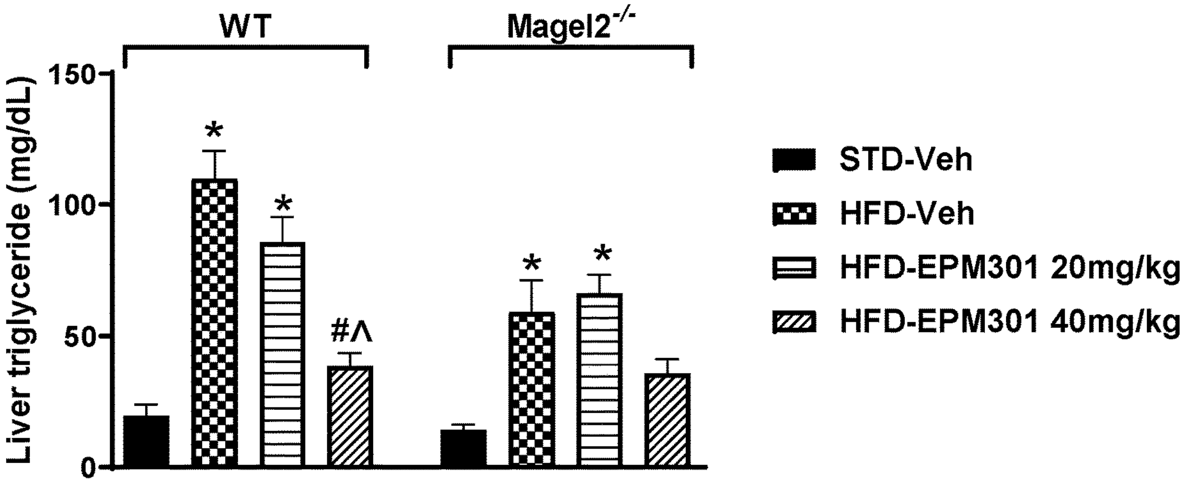
FIGS. 8A-8C show the effect of CBDA-ME on liver triglyceride (FIG. 8A), and liver cholesterol (FIG. 8B) in WT or PWS mouse model fed with high-fat diet (HFD).
Figure 8B:
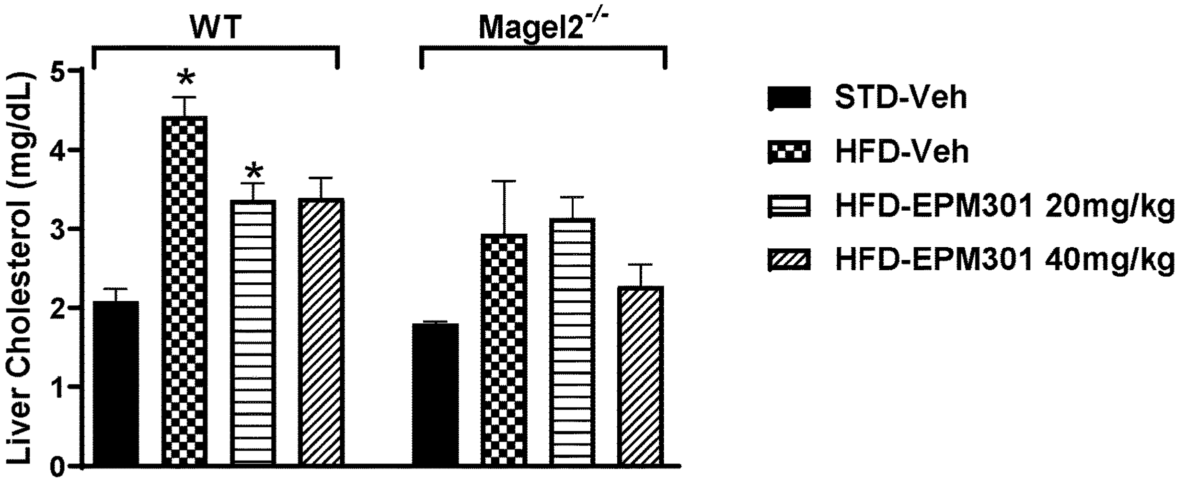
Figure 8C:
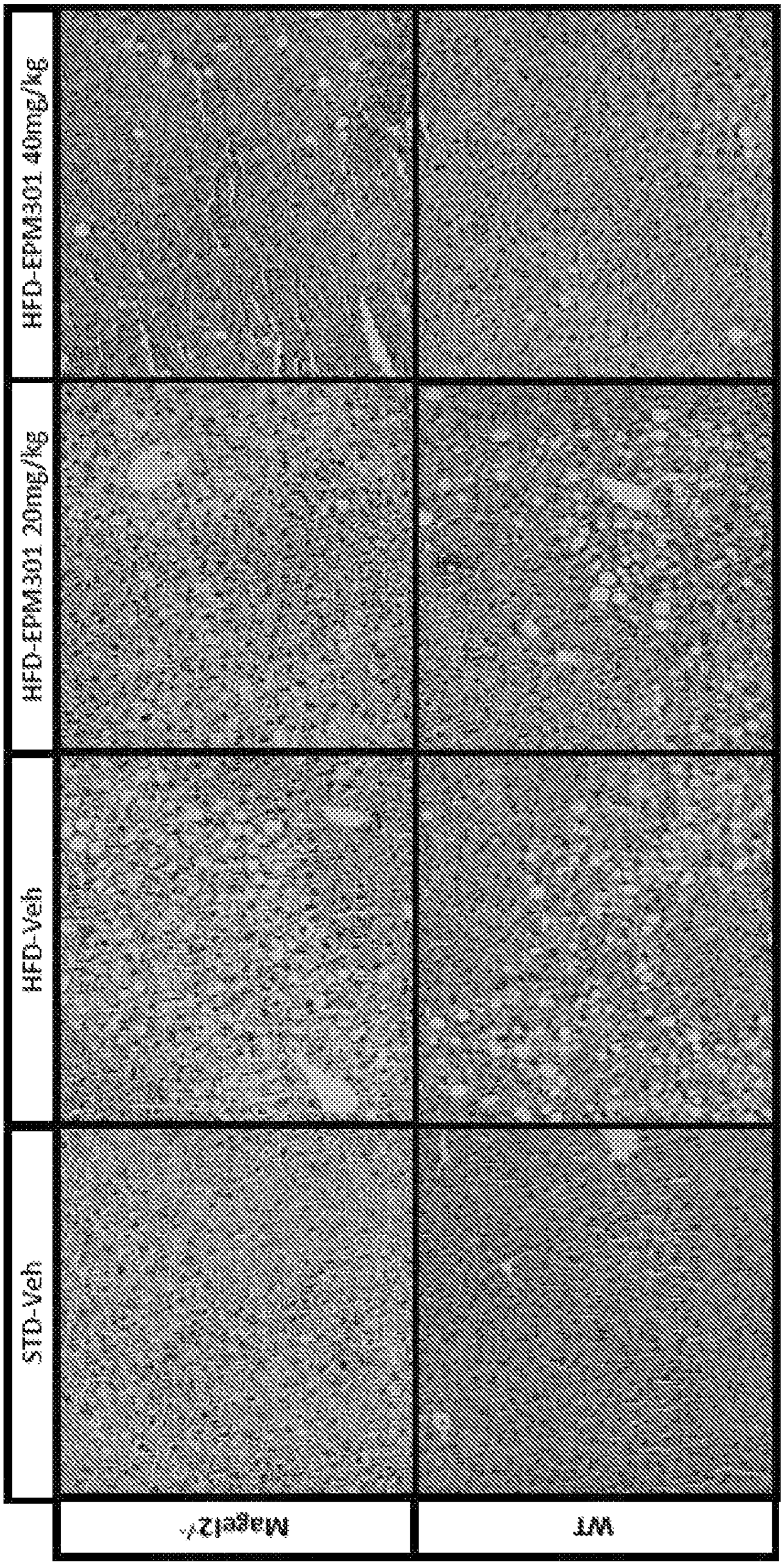

The higher dose of 40 mg/kg CBDA-ME significantly reduced the obesity related hepatocellular injury, as documented by the reduction in the serum levels of AST and ALT. No major changes were documented in ALP levels (FIG. 7A-7C). Similarly, the HFD-induced hepatic steatosis, as reflected by the elevated hepatic triglyceride and cholesterol levels as well as the increased fat vacuoles in the liver, was attenuated by EPM301 (FIG. 8A-C).

Conclusions:

CBDA-ME significantly reduced body weight and food intake (hyperphagia) in Magel2$^{null}$ mice, which are the main metabolic parameters associated with PWS.

CBDA-ME effectively reduced body weight in Magel2$^{null}$ mice in both doses tested, while in WT mice only the higher dose was found effective. CBDA-ME (40 mg/kg) resulted in improvements in almost all parameters measured in WT DIO mice.

Example 4. The Therapeutic Effect of CBDA-ME in a PWS Preventive Model

Study Aim

The aim of the second study was to evaluate whether EPM301 treatment has an impact on body weight gain and adiposity in a mouse model of PWS.

Study Design and Methods

Male 6-week-old Magel2$^{null}$ mice and their wild-type littermate controls were maintained under a 12-h light/dark cycle and fed ad libitum a standard laboratory diet (STD, 14% fat, 24% protein, 62% carbohydrates; NIH-31 rodent diet).

Treatment Groups

Magel2$^{null}$ mice were either treated with EPM301 20 mg/kg/day or with vehicle (1% Tween80, 4% DMSO, 95% Saline). WT siblings were treated with vehicle. All treatments were given for 18 weeks by intraperitoneal (IP) injections.

Results

Figure 9A:
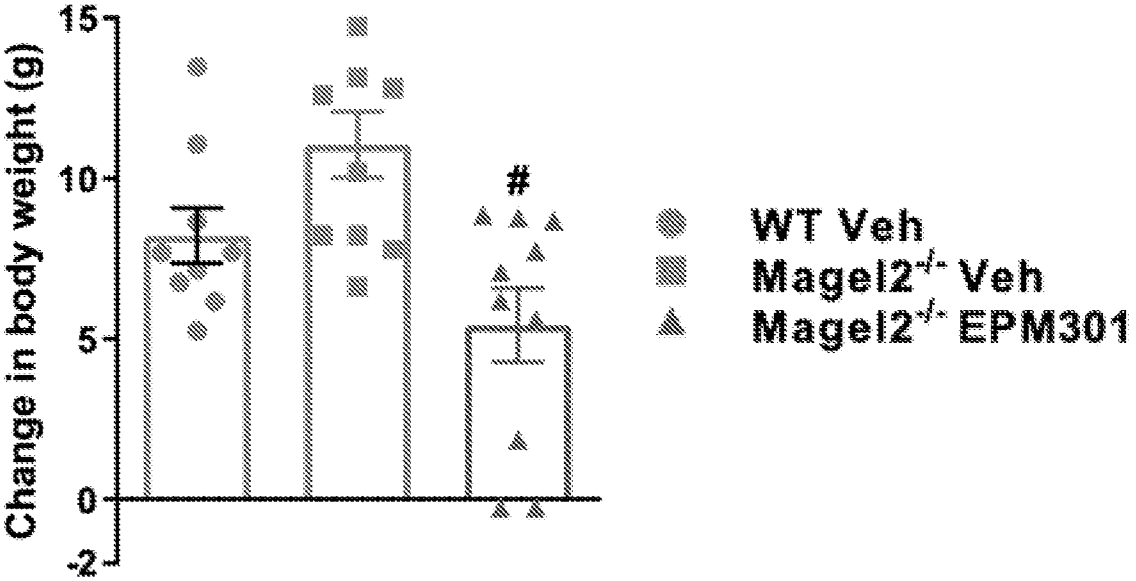
FIGS. 9A-9C show the effect of CBDA-ME in a PWS preventive model on weight gain (FIG. 9A), fat mass (FIG. 9B) and lean mass (FIG. 9C).

Weight Gain:

Results showed that EPM301-treated Magel2$^{null}$ mice had gained weight in a similar manner to the WT control mice, which was lower than the weight gain seen in the vehicle-treated Magel2$^{null}$ mice. When comparing the change in the body weight, the change in Magel2$^{null}$ mice was significantly lower than in the WT controls and the Magel2$^{null}$ vehicle-treated mice (FIG. 9A).

Figure 9B:
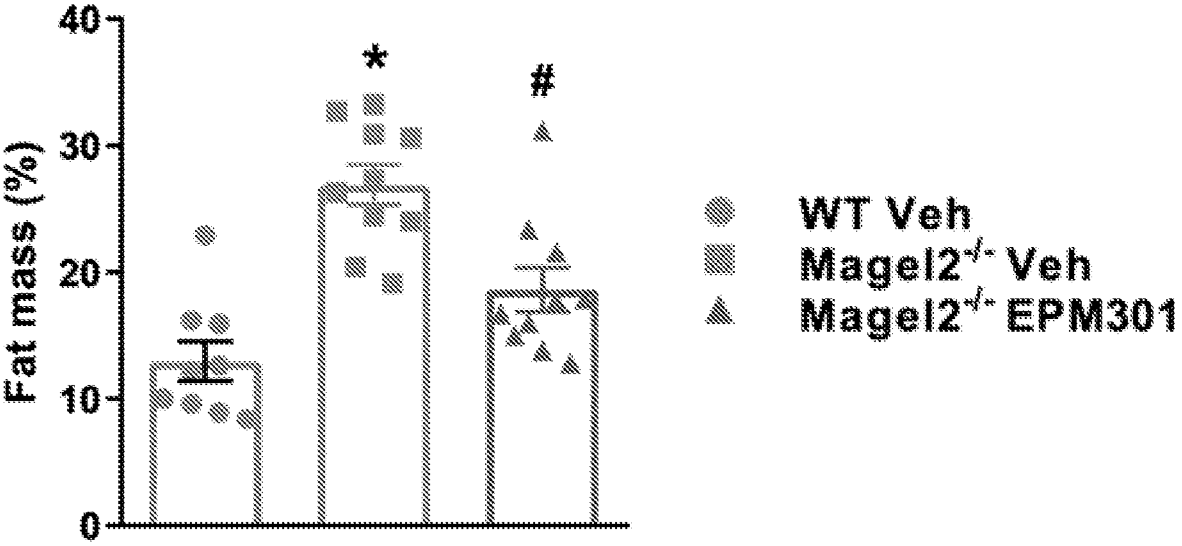

Fat Mass:

Fat mass in the EPM301-treated Magel2$^{null}$ mice was similar to that of the WT control mice, whereas vehicle-treated Magel2$^{null}$ mice had a much higher fat mass, significantly higher than WT control mice. The lower fat mass seen in EPM301-treated Magel2$^{null}$ mice was statistically significant compared to the vehicle-treated Magel2$^{null}$ mice (FIG. 9B).

Figure 9C:
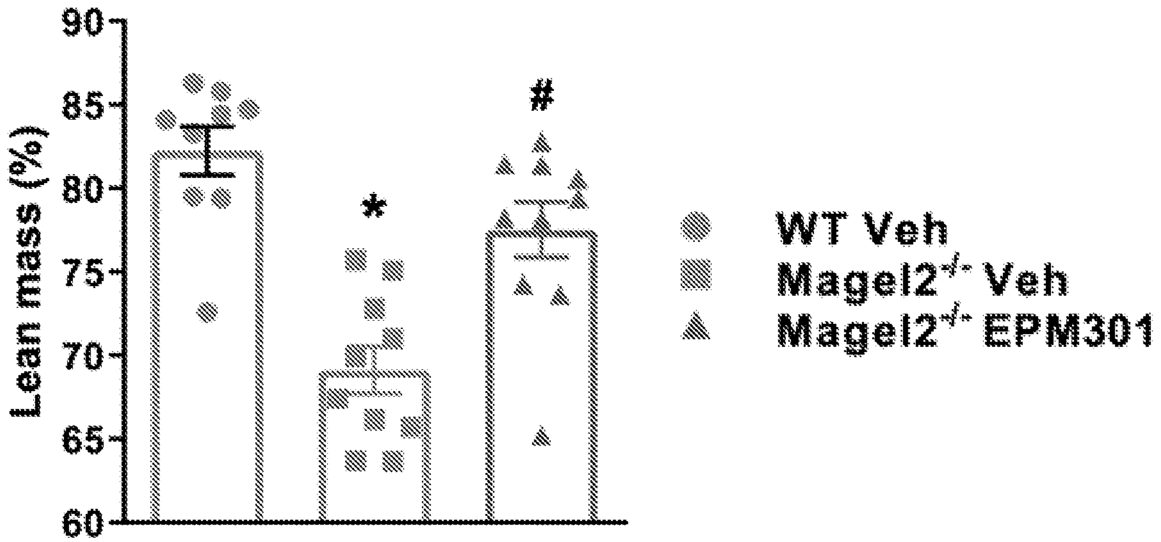

Lean Mass:

The EPM301-treated Magel2$^{null}$ mice had significantly higher lean mass than the vehicle-treated Magel2$^{null}$ mice. The lean mass in the EPM 301-treated Magel2$^{null}$ mice was similar to the WT control mice (FIG. 9C).

CONCLUSIONS

The results showed that EPM301 treatment prevented weight gain, fat mass and increased lean mass in Magel2$^{null}$ mice. These parameters were similar to WT control healthy mice whereas the vehicle-treated Magel2$^{null}$ mice gained more weight, had a much higher fat mass and much lower lean mass.

Although the present invention has been described herein above by way of preferred embodiments thereof, it can be modified, without departing from the spirit and nature of the subject invention as defined in the appended claims.

The invention claimed is:

1. A method for treating Prader Willi Syndrome (PWS), the method comprising:

administering to a subject in need of such treatment a therapeutically effective amount of a pharmaceutical composition comprising a cannabinoid component and a pharmaceutically acceptable carrier, excipient or diluent, wherein the cannabinoid component comprises a cannabidiolic acid (CBDA) ester represented by the structure of Formula (I) alone or in combination with one or more additional cannabinoid compound, Formula (I)

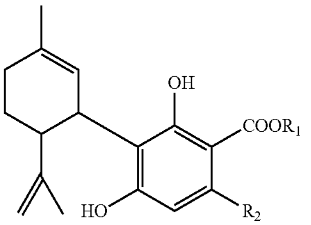

wherein:

$R_1$ and $R_2$ are each independently selected from the group consisting of a linear or branched, unsubstituted or substituted $C_1$-$C_{15}$ alkyl, a linear or branched, unsubstituted or substituted $C_2$-$C_{15}$ alkenyl, and a linear or branched, unsubstituted or substituted $C_2$-$C_{15}$ alkynyl;

and stereoisomers and salts thereof.

2. The method of claim 1, wherein $R_1$ is methyl.

3. The method of claim 1, wherein the cannabidiolic acid ester is CBDA-ME.

4. The method of claim 1, wherein the treating comprises slowing down, preventing progression of, treating or ameliorating one or more symptoms of PWS.

5. The method of claim 1, wherein treating comprises treating behaviors associated with PWS.

6. The method of claim 1, further comprising administering the one or more additional cannabinoid compound.

7. The method of claim 6, wherein the one or more additional cannabinoid compound is selected from the group consisting of cannabidiol (CBD), cannabigerol (CBG), $\Delta^8$-tetrahydrocannabinol ($\Delta^8$-THC), $\Delta^9$-tetrahydrocannabinol ($\Delta^9$-THC), cannabinol (CBN), $\Delta^9$(11)-tetrahydrocannabinol (exo-THC), cannabichromene (CBC), tetrahydrocannabinol-C3 (THC-C3), tetrahydrocannabinol-C4 (THC-C4), tetrahydrocannabinol-C7 (THC-C7), esters thereof and combination thereof.

8. The method of claim 6, wherein the one or more additional cannabinoid compound is obtained from one or more extracts of a cannabis plant.

9. The method of claim 8, wherein the one or more extracts of the cannabis plant comprises at least one cannabinoid selected from the group consisting of CBD, THC, CBN, CBG, CBC, acids thereof, and combination thereof.

10. The method of claim 1, wherein the pharmaceutical composition is in the form of an emulsion, gel, solution, or dispersion.

11. The method of claim 1, wherein the pharmaceutical composition is a dry powder formulation.

12. The method of claim 1, wherein the excipient is selected from the group consisting of triglycerides, fats, lipids, oils, fatty acids, solvents or mixtures thereof.

13. The method of claim 1, wherein the pharmaceutical composition is in the form of a micelle, an emulsion or a liposome.

14. The method of claim 1, wherein the excipient is selected from the group consisting of emulsifiers, buffering agents, pH adjusting agents, preservatives, antioxidants, stabilizers, and a combination thereof.

15. The method of claim 1, wherein the pharmaceutical composition comprising less than about 10% (w/w) of the cannabinoid component.

16. The method of claim 1, wherein treating results in one or more of: (a) decrease in obsessive and compulsive behavior compared to placebo; or (b) decrease in anxiety compared to placebo.

17. The method of claim 1, wherein treating results in a decrease in measurement of Hyperphagia Questionnaire for Clinical Trials (HQ-CT) Total Score.

18. The method of claim 1, further comprising administering to the subject at least one additional therapeutic agent for treatment of PWS.

19. The method of claim 1, wherein administering to a subject in need of such treatment a therapeutically effective amount of a pharmaceutical composition comprises administering the pharmaceutical composition orally, nasally, intravenously, or intramuscularly to the subject.

20. The method of claim 1, wherein administering to a subject in need of such treatment a therapeutically effective amount of a pharmaceutical composition administering the pharmaceutical composition twice a day, once a day, a week, once in two weeks, once in three weeks or once a month to the subject.

* * * * *